United States Patent [19]
Jadhav et al.

[11] Patent Number: 5,637,780
[45] Date of Patent: Jun. 10, 1997

[54] METHOD FOR PREPARING ALKYLATING AGENTS AND THEIR USE FOR ALKYLATING CYCLIC UREAS

[75] Inventors: Prabhakar K. Jadhav; George C. Emmett; Michael E. Pierce, all of Wilmington, Del.

[73] Assignee: The DuPont Merck Pharmaceutical Company, Wilmington, Del.

[21] Appl. No.: 268,610

[22] Filed: Jun. 30, 1994

Related U.S. Application Data

[63] Continuation-in-part of Ser. No. 40,146, Mar. 30, 1993, abandoned.

[51] Int. Cl.$^6$ .......................... C07C 39/28; C07C 31/36; C07D 243/04
[52] U.S. Cl. .......................... 568/841; 568/681; 540/492
[58] Field of Search .................................. 568/681, 841

[56] References Cited

FOREIGN PATENT DOCUMENTS

| 0152174 | 8/1985 | European Pat. Off. | 568/681 |
| 0266544 | 5/1988 | European Pat. Off. | 568/841 |
| WO9307128 | 10/1991 | WIPO | 540/492 |
| WO9323361 | 5/1992 | WIPO | 540/492 |

OTHER PUBLICATIONS

Tet. Letters 42: 4339–4342 (1972).
J. of Organic Chemistry 46: 3361–3364 (1981).
Traylor et al., *J. Amer. Chem. Soc.*, 89, 2304–2316 (1967).
Yamoto et al., *Synthesis*, 1014–1015 (1982).
Costello et al., *Synthetic Commun.*, 17(2), 219–221 (1987).

*Primary Examiner*—Robert T. Bond

[57] ABSTRACT

This invention relates to methods for preparing alkylating agents and use of the agents prepared. In particular, this invention relates to preparation methods for hydroxy halide and organooxy halide alkylating agents and their use for alkylating cyclic urea compounds.

13 Claims, No Drawings

METHOD FOR PREPARING ALKYLATING AGENTS AND THEIR USE FOR ALKYLATING CYCLIC UREAS

CROSS REFERENCE TO EARLIER FILED APPLICATIONS

This application is a continuation-in-part of U.S. patent application Ser. No. 08/040,146 filed Mar. 30, 1993, now abandoned.

FIELD OF THE INVENTION

This invention relates to methods for preparing alkylating agents and use of the agents prepared. In particular, this invention relates to preparation methods for hydroxy halide and organooxy halide alkylating agents and their use for alkylating cyclic urea compounds.

BACKGROUND OF THE INVENTION

Few methods are known for the preparation of hydroxy halide and organooxy halide alkylating agents. Hydroxymethylaryl halides have been prepared from the corresponding aryldimethanols by treatment with hydrogen halides. The reported yields of the desired compounds from aryldimethanols having two equivalent functional groups are generally about 50% or less. For example, Traylor and Ware in *J. Amer. Chem. Soc.* 89, 2304–2316 (1967) report only a 16% yield of p-hydroxymethylbenzyl chloride from 1,4-benzenedimethanol(p-xylene-α,α'-diol). Yamato et al. in *Synthesis*, pp. 1014–1015 (December, 1982) report a 53% yield of o-bromomethylbenzyl alcohol from 1,2-benzenedimethanol.

A 90% yield of 4-hydroxymethyl-2,3,4,5-tetrafluorobenzyl bromide obtained from 1,4-bis(hydroxymethyl)-2,3,4,5-tetrafluorobenzene by treatment with 48% hydrobromic acid was reported by Costello and Milner in *Synthetic Communications*, 17, 219–221 (1987). However, it has since been shown that treatment of benzenedimethanols lacking nuclear halogen substituents shows no particular selectivity, and accordingly, the unusually high yield in this isolated example is believed to be an anomaly due to insolubility of the monohalogenated product in the reaction media.

Lam et al., PCT International Publication Number WO 93/07128 discloses cyclic carbonyl compounds and derivatives thereof which are useful as human immunodeficiency virus (HIV) protease inhibitors for the treatment of HIV infection. The compounds disclosed in WO 93/07128 include cyclic urea compounds of the formula below where W may be —N($R^{22}$)C(=O)N($R^{23}$)—.

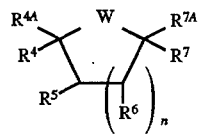

WO 93/07128 discloses compounds wherein groups $R^5$ and $R^6$ may be —O-MEM(MEM=2-methoxyethoxymethyl), —O-SEM (SEM=2-(trimethylsilyl)ethoxymethyl) or —O-MOM (MOM=methoxymethyloxy) or may be taken together to form an acetonide ring. WO 93/07128 also discloses processes for the preparation of alkylated cyclic ureas. The processes of the present invention provide improved alkylating agents and processes for the alkylation of the urea nitrogens to obtain such cyclic urea HIV protease inhibitor compounds.

As disclosed in WO 93/07128, such cyclic urea compounds, which may be made using the processes of the present invention are non-peptidic, low molecular weight, orally bioavailable compounds useful as inhibitors of HIV protease and for the treatment of HIV infection. The HIV protease inhibitory activity of the cyclic urea can be increased by two to three orders of magnitude by alkylating one or both of the urea nitrogens.

Consequently, a need exists for efficient and cost-effective methods for the preparation of the cyclic urea HIV protease inhibitor compounds of WO 93/07128. The present invention provides processes for the preparation of hydroxy halide and organooxy halide alkylating agents in high yields from readily available starting materials. The alkylating agents of the present invention are effective alkylating agents for the alkylation of cyclic urea nitrogens.

SUMMARY OF THE INVENTION

The present invention includes a process for preparing a hydroxy halide alkylating agent or an organooxy halide alkylating agent of formula (I):

 (I)

wherein $R^3$, m, Q, n, and X are defined below, said method comprising the steps of:

(1) reacting an organodiol of formula (II):

 (II)

with a halogenating reagent, to form a compound of formula (IA):

 (IA)

; and (2) reacting compound (IA) with a reagent suitable for the protection of hydroxy groups to form the compound of formula (I) where $R^3$ is a hydroxy protecting group.

The present invention also includes a method for alkylating a cyclic urea compound of formula (IV):

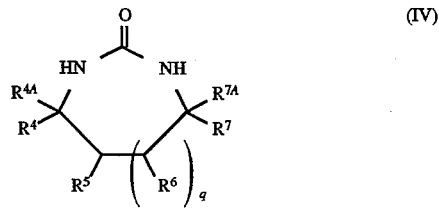 (IV)

wherein $R^4$, $R^{4A}$, $R^5$, $R^{5A}$, q, $R^7$ and $R^{7A}$ are defined below, comprising steps (1) and (2) above and the additional step of:

(3) reacting compound (IV) with compound (I) to form a compound of formula (V):

$$\text{(V)}$$

wherein $R^3$ is a hydroxy protecting group and $R^4$, $R^{4A}$, $R^5$, $R^6$, $R^7$, $R^{7A}$, m, n and q are as defined below.

DETAILED DESCRIPTION OF THE INVENTION

The present invention provides a method for preparing a hydroxy halide alkylating agent or an organooxy halide alkylating agent comprising reacting an organodiol with a halogenating reagent in an aprotic organic solvent, with the proviso that the halogenating reagent is not a hydrogen halide.

The present invention provides a process for preparing a hydroxy halide alkylating agent or an organooxy halide alkylating agent of formula (I):

$$R^3O \underset{m}{\frown} Q \underset{n}{\frown} X \quad \text{(I)}$$

wherein:

Q is selected from the following:
  $C_1-C_8$ alkyl substituted with 0–3 $R^{31}$;
  $C_2-C_8$ alkenyl substituted with 0–3 $R^{31}$;
  $C_2-C_8$ alkynyl substituted with 0–3 $R^{31}$;
  a $C_3-C_{14}$ carbocyclic ring system substituted with 0–5 $R^{31}$ or 0–5 $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is selected independently from:
  cyano, $-CH_2NR^{13}R^{14}$, $-NR^{13}R^{14}$, $-OR^{13}$, $C_2-C_6$ alkoxyalkyl, $-S(O)_mR^{13}$, $-C(=O)NR^{13}R^{14}$, $-NR^{14}C(=O)R^{13}$, $-NR^{14}C(=O)OR^{14}$, $-OC(=O)NR^{13}R^{14}$, $-NR^{13}C(=O)NR^{13}R^{14}$, $-NR^{13}C(=S)NR^{13}R^{14}$, $-NR^{14}SO_2NR^{13}R^{14}$, $-NR^{14}SO_2R^{13}$, $-SO_2NR^{13}R^{14}$, $C_1-C_4$ alkyl, $C_2-C_4$ alkenyl, $C_3-C_{10}$ cycloalkyl, $C_3-C_6$ cycloalkylmethyl, benzyl, phenethyl, phenoxy, benzyloxy, nitro, $C_7-C_{10}$ arylalkyl, formyl, $C_3-C_6$ cycloalkoxy, $C_1-C_4$ alkyl substituted with $-NR^{13}R^{14}$, $C_1-C_4$ alkoxycarbonyl, $C_1-C_4$ alkylcarbonyloxy, $C_1-C_4$ alkylcarbonyl, $-OCH_2CO_2R^{13}$, 2-(1-morpholino)ethoxy, azido, $-C(R^{14})=N(OR^{14})$; or 1–3 amino acids, linked together via amide bonds, said amino acid being linked via the amine or carboxylate terminus;
  a $C_5-C_{14}$ carbocyclic residue substituted with 0–5 $R^{32}$; or
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$ when a substituent on carbon, is selected from one or more of the following:
  phenethyl, phenoxy, $C_3-C_{10}$ cycloalkyl, $C_3-C_6$ cycloalkylmethyl, $C_7-C_{10}$ arylalkyl, benzyl protected oxime, $C_2-C_6$ alkoxyalkyl, methylenedioxy, ethylenedioxy, $C_1-C_4$ alkylcarbonyloxy, $-NHSO_2R^{14}$, benzyloxy, 2-(1-morpholino)ethoxy, $-CONR^{13}NR^{13}R^{14}$, cyano, sulfonamide, $C_3-C_6$ cycloalkoxy, $-NR^{13}R^{14}$, $-C(R^{14})=N(OR^{14})$, $-NO_2$, $-OR^{13}$, $-NR^{40}R^{41}$, $-SR^{13}$, $-SOR^{13}$, $-SO_2R^{13}$, $-SNR^{13}R^{14}$, $-SONR^{13}R^{14}$, $-SO_2NR^{13}R^{14}$, $-C(=O)NR^{13}R^{14}$, $-OC(=O)NR^{13}R^{14}$, $-C(=O)R^{11}$, phenyl, $-C(=O)NR^{13}-(C_1-C_4\text{ alkyl})-NR^{13}R^{14}$, $-C(=O)NR^{40}R^{41}$, $-C(=O)NR^{13}C(R^{11})_2NR^{13}R^{14}$; $-C(=O)NR^{13}C(R^{11})_2NR^{13}CO_2R^{13}$; $-C(=O)NR^{13}-(C_1-C_4\text{ alkyl})-NR^{13}CO_2R^{13}$; $-C(=O)N(R^{13})-(C_1-C_4\text{ alkyl})-R^{11}$; or
  $-C(=O)C(R^{11})_2NR^{13}R^{14}$; $-C(=O)C(R^{11})_2NR^{13}CO_2R^{13}$; $-C(=O)-(C_1-C_4\text{ alkyl})-NR^{13}R^{14}$; $-C(=O)-(C_1-C_4\text{ alkyl})-NR^{13}CO_2R^{13}$; or
  $C_1-C_4$ alkoxy substituted with 0–4 groups selected from: $R^{11}$, $C_3-C_6$ cycloalkyl, $-CO_2R^{13}$, $-C(=O)NR^{13}R^{14}$, $-NR^{13}R^{14}$ or OH;
  $C_1-C_4$ alkyl substituted with 0–4 groups selected from: $R^{11}$, $=NR^{14}$, $=NNR^{13}C(=O)NR^{13}R^{14}$, $=NNR^{13}C(=O)OR^{13}$, or $-NR^{13}R^{14}$;
  $C_2-C_4$ alkenyl substituted with 0–4 $R^{11}$;
  $C_2-C_4$ alkynyl substituted with 0–4 $R^{11}$;
  a 5- or 6-membered heterocyclic ring containing from 1 to 4 heteroatoms independently selected from oxygen, nitrogen or sulfur, substituted with 0–2 $R^{12}$;
  or $R^{32}$ may be a 3- or 4- carbon chain attached to adjacent carbons on the ring to form a fused 5- or 6-membered ring, said 5- or 6-membered ring being optionally substituted on the aliphatic carbons with halogen, $C_1-C_4$ alkyl, $C_1-C_4$ alkoxy, benzyloxy, or $-NR^{13}R^{14}$; or, when $R^{32}$ is attached to a saturated carbon atom, it may be $=O$, $=S$, $=NO\text{-benzyl}$; or when $R^{32}$ attached to sulfur it may be $=O$;

$R^{32}$, when a substituent on nitrogen, is selected from one or more of the following: phenyl, benzyl, phenethyl, benzyloxy, $C_1-C_4$ benzyloxyalkyl, $C_1-C_4$ alkoxy, $C_1-C_4$ alkyl, $C_3-C_6$ cycloalkyl, $C_3-C_6$ cycloalkylmethyl, $-CH_2NR^{13}R^{14}$, $-NR^{13}R^{14}$, $C_2-C_6$ alkoxyalkyl, $C_1-C_4$ alkylcarbonyl, $-C(R^{14})=N(OR^{14})$;

$R^{40}$ is selected from: H, $C_1-C_3$ alkyl;

$R^{41}$ is selected from:
  $-C(=O)NR^{13}R^{14}$;
  $-C(=O)NR^{13}NR^{13}R^{14}$;
  $-C(=O)C(R^{11})_2NR^{13}R^{14}$;
  $-C(=O)C(R^{11})_2NR^{13}NR^{13}R^{14}$;
  $-C(=O)C(R^{11})_2NR^{13}CO_2R^{13}$;
  $-C(=O)H$;
  $-C(=O)R^{11}$;
  $-C(=O)-(C_1-C_4\text{ alkyl})-NR^{13}R^{14}$;
  $-C(=O)-(C_1-C_4\text{ alkyl})-NR^{13}CO_2R^{13}$;
  1–3 amino acids linked together via amide bonds, and linked to the N atom via the carboxylate terminus;

$R^{11}$ is selected from one or more of the following:
  H, keto, cyano, $-CH_2NR^{13}R^{14}$, $-NR^{13}R^{14}$, $-OR^{13}$, $-S(O)_mR^{13}$, $-NR^{14}C(=O)R^{13}$, $=NOR^{14}$, $-NR^{14}C(=O)OR^{14}$, $-OC(=O)NR^{13}R^{14}$, $-NR^{13}C(=O)NR^{13}R^{14}$, $-NR^{14}SO_2NR^{13}R^{14}$, $-NR^{14}SO_2R^{13}$, $-SO_2NR^{13}R^{14}$, $-OP(O)(OR^{13})_2$, $C_1-C_4$ alkyl, $C_2-C_4$ alkenyl, $C_3-C_6$ cycloalkylmethyl, benzyl, phenethyl, phenoxy, benzyloxy, nitro, $C_7-C_{10}$ arylalkyl, formyl, $C_3-C_6$ cycloalkoxy, $C_3-C_4$ alkyl substituted with $-NR^{13}R^{14}$, $C_1-C_4$ benzyloxyalkyl, methylenedioxy, ethylenedioxy, $C_1$–$C_4$ alkylcarbonyl, $C_1$–$C_4$ alkylcarbonylamino, 2-(1-morpholino)ethoxy, azido, or —C($R^{14}$)=N(O$R^{14}$);

1–3 amino acids linked together via amide bonds, said amino acid being linked via the amine or carboxylate terminus;

$C_3$–$C_{10}$ cycloalkyl substituted with 0–2 $R^{12}$;

$C_1$–$C_4$ alkyl substituted with 0–2 $R^{12}$ aryl($C_1$–$C_3$ alkyl)-, substituted with 0–2 $R^{12}$;

$C_2$–$C_6$ alkoxyalkyl-, substituted with 0–2 $R^{12}$;

$C_1$–$C_4$ alkylcarbonyloxy substituted with 0–2 $R^{12}$, $C_6$–$C_{10}$ arylcarbonyloxy substituted with 0–2 $R^{12}$, a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:

H, keto, cyano, —CH$_2$N($R^{13A}$)R$^{(14A)}$, —N($R^{13A}$)R$^{(14A)}$, —CO$_2$H, —OC(=O)($C_1$–$C_3$ alkyl), —Obenzyl, $C_2$–$C_6$ alkoxyalkyl, —C(=O)NH$_2$, —OC(=O)NH$_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is selected from one or more of the following:

phenyl, benzyl, phenethyl, phenoxy, benzyloxy, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —O$R^{13}$, $C_1$–$C_4$ alkyl substituted with —N$R^{13}R^{14}$, —N$R^{13}R^{14}$, $C_2$–$C_6$ alkoxyalkylene optionally substituted with —Si(CH$_3$)$_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S$R^{13}$, —SO$R^{13}$, —SO$_2R^{13}$, —SO$_2$N$R^{13}R^{14}$, —NHSO$_2R^{14}$, —OCH$_2$CO$_2R^{13}$, 2-(1-morpholino)ethoxy, —C($R^{14}$)=N(O$R^{14}$); or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, hydroxy, or —N$R^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$N$R^{13}R^{14}$, —N$R^{13}R^{14}$, $C_2$–$C_6$ alkoxyalkyl, $C_1$–$C_4$ alkylcarbonyl, —C($R^{14}$)=N(O$R^{14}$);

$R^{12A}$, when a substituent on carbon, is selected from one or more of the following:

phenyl, benzyl, phenethyl, phenoxy, benzyloxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —O$R^{13}$, $C_2$–$C_6$ alkoxyalkyl optionally substituted with —Si(CH$_3$)$_3$, $C_1$–$C_4$ benzyloxyalkyl, methylenedioxy, ethylenedioxy, $C_1$–$C_4$ alkylcarbonyl, $C_1$–$C_4$ alkylcarbonylamino, —SMe, —S(=O)Me, —SO$_2$Me, —OCH$_2$CO$_2R^{13}$, 2-(1-morpholino)ethoxy; or a 5- or 6-membered heterocyclic ring containing from 1 to 4 heteroatoms independently selected from oxygen, nitrogen or sulfur;

or $R^{12A}$ may be a 3- or 4- carbon chain attached to adjacent carbons on the ring to form a fused 5- or 6-membered ring, said 5- or 6-membered ring being optionally substituted on the aliphatic carbons with $C_1$–$C_4$ alkyl, $C_1$—$C_4$ alkoxy, benzyloxy; or, when $R^{12A}$ is attached to a saturated carbon atom, it may be =O or =S; or when $R^{12}$ is attached to sulfur it may be =O;

$R^{12}$A, when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ alkylcarbonyl;

$R^{13}$ is selected from:

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_1$–$C_6$ alkylcarbonyl substituted with 0–3 $R^{11A}$;

$C_1$–$C_6$ alkoxycarbonyl substituted with 0–3 $R^{11A}$;

$C_1$–$C_6$ alkylaminocarbonyl substituted with 0–3 $R^{11A}$;

$C_3$–$C_6$ alkoxyalkyl substituted with 0–3 $R^{11A}$;

an amine protecting group when $R^{13}$ is bonded to N;

a hydroxy protecting group when $R^{13}$ is bonded to O;

$R^{14}$ is benzyloxy, $C_1$–$C_6$ alkyl substituted with 0–3 groups selected from -Obenzyl, $C_1$–$C_4$ alkoxy, $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —(CH$_2$)$_4$—, —(CH$_2$)$_5$—, —CH$_2$CH$_2$N($R^{15}$)CH$_2$CH$_2$—, or —CH$_2$CH$_2$OCH$_2$CH$_2$—;

$R^{13A}$ and $R^{14A}$ are independently selected from: H, $C_1$–$C_6$ alkyl;

$R^{13A}$ and $R^{14A}$ can alternatively join to form —(CH$_2$)$_4$—, —(CH$_2$)$_5$—, —CH$_2$CH$_2$N($R^{15}$)CH$_2$CH$_2$—, or —CH$_2$CH$_2$OCH$_2$CH$_2$—;

$R^{15}$ is H or CH$_3$;

X is chloro, bromo or iodo;

$R^3$ is a hydroxy protecting group; and m and n are independently 1, 2 or 3;

said process comprising the steps of:

(1) reacting an organodiol of formula (II):

wherein Q, m and n are as defined above for formula (I), with a halogenating reagent in an aprotic organic solvent, preferably in a chlorinated organic solvent, with the proviso that the halogenating reagent is not a hydrogen halide, to form a compound of formula (IA):

$$HO\underset{(\ )_m}{\diagdown}Q\underset{(\ )_n}{\diagdown}X, \quad (IA)$$

wherein Q, X, m, and n are as defined above for formula (I); and (2) reacting compound (IA) with a reagent suitable for the protection of hydroxy groups to form the compound of formula (I) wherein $R^3$ is a hydroxy protecting group.

In a preferred process of the present invention for the preparation of alkylating agents of formula (I) described above, the compound of formula (I) is obtained by carrying out steps (1) and (2) without isolation of the compound of formula (IA).

Preferred in the present invention is a process for preparing an alkylating agent compound of formula (I) as described above wherein:

Q is selected from:
  $C_1$–$C_8$ alkyl substituted with 0–3 $R^{31}$;
  $C_2$–$C_8$ alkenyl substituted with 0–3 $R^{31}$;
  $C_2$–$C_8$ alkynyl substituted with 0–3 $R^{31}$;
  a $C_3$–$C_{14}$ carbocyclic ring system substituted with 0–5 $R^{31}$ or 0–5 $R^{32}$;

$R^{31}$ is selected from one or more of the following:
  cyano, —$CH_2NR^{13}R^{14}$, —$NR^{13}R^{14}$, —$OR^{13}$, $C_2$–$C_6$ alkoxyalkyl, —$SR^{13}$, —$SOR^{13}$, —$SO_2R^{13}$ $C_1$–$C_4$, alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, formyl, $C_3$–$C_6$ cycloalkoxy, $C_1$–$C_4$ alkyl substituted with —$NR^{13}R^{14}$, $C_1$–$C_4$ alkoxycarbonyl, $C_1$–$C_4$ alkylcarbonyloxy, $C_1$–$C_4$ alkylcarbonyl, —$OCH_2CO_2R^{13}$, 2-(1-morpholino)ethoxy, azido, —$C(R^{14})=N(OR^{14})$; or
  a $C_5$–$C_{14}$ carbocyclic residue substituted with 0–5 $R^{32}$; or
  aryl substituted with 0–3 $R^{32}$; or
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
  phenethyl, phenoxy, $C_3$–$C_{10}$ cycloalkyl, $C_3$–$C_6$ cycloalkylmethyl, $C_7$–$C_{10}$ arylalkyl, benzyl protected oxime, $C_2$–$C_6$ alkoxyalkyl, methylenedioxy, ethylenedioxy, $C_1$–$C_4$ alkylcarbonyloxy, —$NHSO_2R^{14}$, benzyloxy, 2-(1-morpholino)ethoxy, —$CONR^{13}NR^{13}R^{14}$, cyano, sulfonamide, $C_3$–$C_6$ cycloalkoxy, —$NR^{13}R^{14}$, —$C(R^{14})=N(OR^{14})$, —$NO_2$, —$OR^{13}$, —$NR^{40}R^{41}$, —$SO_pR^{13}$, —$SNR^{13}R^{14}$, —$SONR^{13}R^{14}$, —$SO_2NR^{13}R^{14}$, 13 $C(=O)NR^{13}R^{14}$, —$OC(=O)NR^{13}R^{14}$, —$C(=O)R^{11}$, phenyl, —$C(=O)NR^{13}$—($C_1$–$C_4$ alkyl)-$NR^{13}R^{14}$, —$C(=O)NR^{40}R^{41}$;
  —$C(=O)NR^{13}C(R^{11})_2NR^{13}R^{14}$;
  —$C(=O)NR^{13}C(R^{11})_2NR^{13}CO_2R^{13}$;
  —$C(=O)NR^{13}$—($C_1$–$C_4$ alkyl)-$NR^{13}CO_2R^{13}$;
  —$C(=O)N(R^{13})$—($C_1$–$C_4$ alkyl)-$R^{11}$; or
  —$C(=O)C(R^{11})_2NR^{13}R^{14}$;
  —$C(=O)C(R^{11})_2NR^{13}CO_2R^{13}$; —$C(=O)$—($C_1$–$C_4$ alkyl)-$NR^{13}R^{14}$; —$C(=O)$—($C_1$–$C_4$ alkyl)-$NR^{13}CO_2R^{13}$; or
  $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or benzyloxy;
  $C_1$–$C_4$ alkyl substituted with 0–4 groups selected from: $R^{11}$, =$NR^{14}$, =$NNR^{13}C(=O)NR^{13}R^{14}$, or —$NR^{13}R^{14}$;
  $C_2$–$C_4$ alkenyl substituted with 0–4 $R^{11}$;
  $C_2$–$C_4$ alkynyl substituted with 0–4 $R^{11}$;
  a 5- or 6-membered heterocyclic ring containing from 1 to 4 heteroatoms independently selected from oxygen, nitrogen or sulfur, substituted with 0–2 $R^{12}$;
  or $R^{32}$ may be a 3- or 4- carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, benzyloxy, or —$NR^{13}R^{14}$; or, when $R^{32}$ is attached to a saturated carbon atom, it may be =O, =S, =NO-benzyl; or when $R^{32}$ attached to sulfur it may be =O;

$R^{32}$, when a substituent on nitrogen, is selected from one or more of the following:
  phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C2$–$C_6$ alkoxyalkyl, $C_1$–$C_4$ alkylcarbonyl, —$C(R^{14})=N(OR^{14})$;

$R^{40}$ is selected from: H, $C_1$–$C_3$ alkyl;

$R^{41}$ is selected from:
  —$C(=O)NR^{13}R^{14}$;
  —$C(=O)NR^{13}NR^{13}R^{14}$;
  —$C(=O)C(R^{11})_2NR^{13}R^{14}$;
  —$C(=O)C(R^{11})_2NR^{13}NR^{13}R^{14}$;
  —$C(=O)C(R^{11})_2NR^{13}CO_2R^{13}$;
  —$C(=O)H$;
  —$C(=O)R^{11}$;
  —$C(=O)$—($C_1$–$C_4$ alkyl)-$NR^{13}R^{14}$;
  —$C(=O)$—($C_1$–$C_4$ alkyl)-$NR^{13}CO_2R^{13}$;
  1–3 amino acids linked together via amide bonds, and linked to the N atom via the carboxylate terminus;

$R^{11}$ is selected from one or more of the following:
  H, keto, cyano, —$CH_2NR^{13}R^{14}$, —$NR^{13}R^{14}$, —$OR^{13}$, —$SR^{13}$, —$SOR^{13}$, —$SO_2R^{13}$, $C_1$–$C_4$ alkyl, $C_2$–$C_4$ alkenyl, $C_3$–$C_{10}$ cycloalkyl substituted with 0–2 $R^{12}$, a $C_5$–$C_{14}$ carbocyclic residue substituted with 0–3 $R^{12}$, aryl($C_1$–$C_3$ alkyl)-, substituted with 0–2 $R^{12}$, aryl substituted with 0–3 $R^{12}$; or
  a 5- to 10-membered heterocyclic ring system containing 1 to 4 heteroatoms independently selected from oxygen, nitrogen or sulfur, said heterocyclic ring system being substituted with 5 0–3 $R^{12}$;

$R^{12}$, when a substituent on carbon, is selected from one or more of the following:
  phenyl, benzyl, phenethyl, phenoxy, benzyloxy, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl optionally substituted with —$Si(CH_3)_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$SR^{13}$, —$SOR^{13}$, —$SO_2R^{13}$, —$SO_2NR^{13}R^{14}$, —$NHSO_2R^{14}$, 2-(1-morpholino)ethoxy, —$C(R^{14})=N(OR^{14})$; or
  a 5- or 6-membered heterocyclic ring containing from 1 to 4 heteroatoms independently selected from oxygen, nitrogen or sulfur;
  or $R^{12}$ may be a 3- or 4- carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, hydroxy, or —$NR^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:
phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkylcarbonyl, —$C(R^{14})$=$N(OR^{14})$;

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

$R^{15}$ is H or $CH_3$;

X is chloro, bromo or iodo;

$R^3$ is a hydroxy protecting group;

m and n are independently 1, 2 or 3.

More preferred in the present invention is a process for preparing an alkylating agent compound of the formula (I) as described above wherein:

Q is selected from:
allyl, methyl, ethyl, propyl, cyclopropylmethyl, n-butyl, i-butyl, $CH_2CH$=$C(CH_3)_2$, pyridinylmethyl, methallyl, n-pentyl, i-pentyl, hexyl, phenyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorophenyl, quinolinylmethyl, carboxyphenyl, benzyloxyphenyl, phenylphenyl, adamantylethyl, cyclopropylmethoxyphenyl, methoxyphenyl, methylphenyl, ethoxyphenyl, benzyloxymethylphenyl, N-protected aminophenyl, formylphenyl, cyanophenyl, cinnamyl, allyloxyphenyl, fluorophenyl, difluorophenyl, fluoromethylphenyl, cyclobutylmethyl, cyclopentylmethyl, nitrophenyl, ($H_2NC$(=O))-phenyl, carbomethoxyphenyl, carboethoxyphenyl, tetrazolylphenyl, and dimethylallyl, N-protected aminomethylphenyl, (O-benzylformaldoxime) phenyl, (O-methylformaldoxime)phenyl, ($CH_3O_2CO$)-phenyl, (benzyl-$OCH_2CH_2N$=CH)-phenyl, N-benzylaminocarbonylphenyl, N-protected N-methylaminophenyl, N-protected N-ethylaminophenyl, N-protected N-ethylaminomethylphenyl, acetylphenyl, acetoxyphenyl, N-benzyloxylaminophenyl, N-benzyloxylaminomethylphenyl, (benzyloxyl) ethylphenyl, ($CH_3C$(=NO-benzyl))-phenyl, ($H_2NNHC$(=O))-phenyl, ($H_2NC$(=O)NHN=CH)-phenyl, ($CH_3ONHC$(=O))-phenyl, (HONHC(=O))-phenyl, ($CH_3NHC$(=O))-phenyl, N,N-dimethylaminocarbonylphenyl, (benzyl-$OCH_2CH$(OH)$CH_2O$)-phenyl, benzyloxyethoxyphenyl, (oxazolidinyl)-phenyl, (benzyloxyl)hexyl, hexenyl, (benzyloxy)octyl, (benzyloxyl)pentyl, (carboxy) pentyl, (carbomethoxy)pentyl, (methylthio)phenyl, (methylsulfonyl)phenyl, N,N-dimethylaminomethylphenyl, N-protected N-methylaminomethylphenyl, glycylaminophenyl, N,N-dimethylglycylaminophenyl, alanylaminophenyl, (N-phenylmethoxycarbonyl) alanylaminophenyl, phenylalanylaminophenyl, (N-phenylmethoxycarbonyl) phenylalanylaminophenyl, ($CH_3CH_2NHC$(=O))-phenyl, N,N-diethylaminocarbonylphenyl, N-ethylaminocarbonylphenyl, N-propylaminocarbonylphenyl, N,N-diisopropylaminocarbonylphenyl, N,N-di-n-propylaminocarbonylphenyl, (benzyloxypropynyl) phenyl, (imidazolyl-C(=O))-phenyl, (pyrazolyl-C (=O))-phenyl, (pyridylmethylaminocarbonyl) phenyl, (oxadiazolidinonyl)phenyl, trifluoroacetylphenyl, (pyrazolyl)phenyl, ($H_2NSO_2$)-phenyl, dibenzyloxyethylphenyl, (MeHNC(=O) NH)-phenyl, ($H_2NC$(=O)NH)-phenyl, (HC(=O) NH)-phenyl, methanesulfonylpentyl, methoxypentyl, N-formyl-N-methylaminophenyl, acetylaminophenyl, propionylphenyl, butyrylphenyl, ($CH_3CH_2C$(=NObenzyl))-phenyl, (trifluorohydroxyethyl)phenyl, ($CF_3C$(=NOH))-phenyl, (N-methylglycyl)aminophenyl, ((4-morpholino)ethyl)aminocarbonylphenyl, (N,N-dimethylaminoethyl)aminocarbonylphenyl, (N,N-diethylaminoethyl)aminocarbonylphenyl, (4-methylpiperazin-1-ylethyl)aminocarbonylphenyl, (benzyl-NHC(=O)O)phenyl, ($CH_3NHC$(=O)O) phenyl, ($NH_2C$(=O)$CH_2O$)phenyl, ($NH_2C$(=NH)) phenyl, ((N-phenylmethoxycarbonyl)glycylamino) phenyl, (imidazolylmethyl)phenyl, (($CH_3$)$_3C$—C (=O))phenyl, (N-methyl-N-ethylaminoethyl) aminocarbonylphenyl, (pyrrolidinylethyl) aminocarbonylphenyl, (piperidinylethyl) aminocarbonylphenyl, ($H_2NC$(=NObenzyl)) phenyl, ($H_2NC$(=NObenzyl))fluorophenyl, benzimidazolylmethyl, benzotriazolylmethyl, indazolylmethyl, benzoxazolinylmethyl, benzisoxazolylmethyl, thienylmethyl, or furylmethyl;

m and n are independently 1, 2 or 3;

X is chloro, bromo or iodo;

$R^3$ is a hydroxy protecting group.

Further preferred in the present invention is the above process for preparing an alkylating agent compound of formula (I) wherein:

Q is selected from:
allyl, propyl, cyclopropylmethyl, n-hexyl, n-butyl, $CH_2CH$=$C(CH_3)_2$, methallyl, i-pentyl, phenyl, hexyl, isoprenyl, cinnamyl, fluorophenyl, (methylsulfonyl)phenyl, cyclopropylmethyl, naphthylmethyl, 4-pyridinylmethyl, 2-pyridinylmethyl, carboxypentyl, cyclopentylmethyl, cyanophenyl, quinolinylmethyl, vinylphenyl, methylphenyl, carbomethoxyphenyl, formylphenyl, (O-benzylformaldoxime)phenyl, cyclobutylmethyl, difluorophenyl, nitrophenyl, N-protected aminomethylphenyl, 3-(NHCHO) phenyl, benzyloxyphenyl, N-benzyloxylaminomethylphenyl, 3-($CH_3OC$(=O)) O—)phenyl, 3-(1-benzyloxyethyl)phenyl, 3-($HOCH_2CH_2N$=CH)phenyl, 3-(2-oxazolidinyl) phenyl, 3-($C_6H_5CH_2NHC$(=O)O)phenyl, 3-($CH_3NHC$(=O)O)phenyl, acetylphenyl, ($CH_3C$ (=NO-benzyl))-phenyl, 2-(hydroxymethyl)-cyclopropylmethyl, ($H_2NNHC$(=O))-phenyl, ($H_2NC$(=O)NHN=CH)-phenyl, 3-[(N-methoxy) aminocarbonyl]-phenyl, 4-[(N-methoxy)

aminocarbonyl]-phenyl, benzyloxyethoxyphenyl, (benzyl-OCH₂CH(Obenzyl)CH₂O)-phenyl, (NH₂C(=NH))phenyl, (methylaminocarbonyl)phenyl, 3-formyl-phenyl, 3-(1-benzyloxyethyl)phenyl, (methylaminocarbonyl)phenyl, (H₂NC(=O)NH)-phenyl, N-protected N-methylaminophenyl, N-protected aminophenyl, N,N-dimethylaminophenyl, 3-propionylphenyl, (CH₃NHC(=O)NH)-phenyl, 3-(2-imidazolyl-C(=O))phenyl, 3-(CH₃CH₂C(=N-O-benzyl))phenyl, N,N-dimethylglycylaminophenyl, 3-((N-phenylmethoxycarbonylaminoglycyl)amino)phenyl, 3-((N-phenylmethoxycarbonylamino-L-alanyl)amino)phenyl, 3-((N-phenylmethoxycarbonylamino-L-phenylalanyl)amino)phenyl, 3-(CF₃CH₂C(=N-Obenzyl))phenyl, alanylaminophenyl, phenylalanylaminophenyl, (methylsulfonyl)pentyl, N-protected N-ethylaminocarbonylphenyl, 3-(N-imidazolylmethyl)phenyl, 3-(2,2,2-trifluoro-1-hydroxyethyl)phenyl, N-diethylaminocarbonylphenyl, N-protected N-propylaminocarbonylphenyl, pyridinylmethyl, aminocarbonylphenyl, 3-(H₂NC(=NObenzyl)-4-fluorophenyl, 3-(5-methyl-1,2,3-oxadiazolyl)phenyl, 3-(H₂NC(=NObenzyl)-4-fluorophenyl, benzimidazolylmethyl, benzotriazolylmethyl, indazolylmethyl, N-protected 3-ethylamino-5-indazolylmethyl, or 3-amino-5-benzisoxazolylmethyl;

m and n are independently 1, 2 or 3;

X is chloro, bromo or iodo; and

R³ is a hydroxy protecting group.

Also preferred is the above process wherein R³ is selected from: triphenylmethyl, tetrahydropyranyl, tetrahydrofuranyl, or t-butyl.

Also preferred in the present invention is the above process for preparing an alkylating agent of formula (I) wherein:

Q is selected from:
  phenyl substituted with 0–2 R³¹;
  naphthyl substituted with 0–2 R³¹;
  pyridyl substituted with 0–2 R³¹;
  pyrimidyl substituted with 0–2 R³¹;
  straight-chain or branched alkyl of 1–6 carbons, substituted with 0–2 R³¹;

R³¹ at each occurence is independently selected from:
  hydrogen, chloro, bromo, fluoro, alkyl of 1–3 carbons, OR¹³, nitro, CF₃, cyano or N(R¹³)(R¹⁴);

R¹³ and R¹⁴ are independently selected from hydrogen or alkyl of 1–6 carbon atoms;

R³ is a hydroxy protecting group; and

X is chloro, bromo or iodo;

m and n are independently 1, 2 or 3.

Also preferred in the present invention is a process for preparing a hydroxy halide alkylating agent or an organooxy halide alkylating agent of formula (Ia):

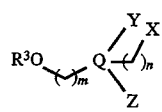  (Ib)

wherein:

Q is phenyl, naphthyl, pyridyl, pyrimidyl or straight-chain or branched alkyl of 1–6 carbons;

X is chloro, bromo or iodo;

Y and Z are independently hydrogen, chloro, bromo, fluoro, alkyl of 1–3 carbons, OR¹ᴬ, nitro, CF₃, cyano or N(R¹ᴬ)(R²ᴬ); where R¹ᴬ and R²ᴬ independently are hydrogen or alkyl of 1–6 carbon atoms;

R³ is a hydroxy protecting group; and m and n are independently 1, 2 or 3;

comprising the steps of:

(1) reacting an organodiol of formula (IIb):

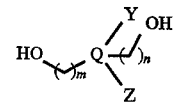  (IIb)

wherein Q, Y, Z, m and n are defined as for formula (Ib), with a halogenating reagent in a chlorinated organic solvent, with the proviso that the halogenating reagent is not a hydrogen halide, to form a compound of formula (IAb):

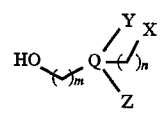  (IAb)

where Q, X, Y, Z, m and n are defined as for formula (Ib); and (2) reacting compound (IAb) with a reagent suitable for protecting hydroxy groups to form the compound of formula (Ib), where R³ is a hydroxy protecting group.

Another aspect of the invention is a method for alkylating a cyclic urea compound of formula (IV):

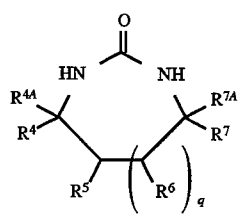  (IV)

wherein:

R⁴ and R⁷ are independently selected from the following groups:
  hydrogen;
  C₁–C₈ alkyl substituted with 0–3 R¹¹;
  C₂–C₈ alkenyl substituted with 0–3 R¹¹;
  C₂–C₈ alkynyl substituted with 0–3 R¹¹;
  a C₃–C₄ carbocyclic ring system substituted with 0–3 R¹¹ or 0–3 R¹²;
  a 5- to 10-membered heterocyclic ring system containing 1 to 4 heteroatoms independently selected from oxygen, nitrogen or sulfur, said heterocyclic ring system being substituted with 0–2 R¹²;
  —OR¹³; —SR¹³;

R⁴ᴬ and R⁷ᴬ are independently selected from the following groups:
  hydrogen;
  C₁–C₄ alkyl substituted with 0–3 C₁–C₂ benzyloxy;
  benzyl substituted with 0–3 C₁–C₂ alkoxy;
  —OR¹³; —SR¹³;

R⁴ and R⁴ᴬ can alternatively join to form a 5–7 membered carbocyclic ring substituted with 0–2 R¹²;

R⁷ and R⁷ᴬ can alternatively join to form a 5–7 membered carbocyclic ring substituted with 0–2 R¹²;

q is 0, 1, or 2;

$R^5$ is selected from H; fluorine; $C_1$–$C_6$ alkyl substituted with 0–3 $R^{11}$; —N($R^{20}$)$_2$; —S$R^{20}$; or —O$R^{20}$, —N$_3$;

$R^6$ is independently selected from: hydrogen, fluorine, $C_1$–$C_6$ alkyl substituted with 0–3 $R^{11}$, —N($R^{20}$)$_2$, —S$R^{20}$, or —O$R^{21}$, —N$_3$;

$R^5$ and $R^6$ can alternatively join to form an epoxide or aziridine ring; a cyclic hydroxyl protecting group; —OCH$_2$SCH$_2$O—; —OC($R^1$)($R^2$)O—; —OC(=S)O—; —OC(=O)C(=O)O—; —OC(CH$_3$)$_2$O—; —OC(OCH$_3$)(CH$_2$CH$_2$CH$_3$)O—; or any group that, when administered to a mammalian subject, cleaves to form a free dihydroxyl or diamino or hydroxyl and amino;

$R^1$ and $R^2$ are independently H, $C_1$–$C_4$ alkyl, $C_1$–$C_4$ alkoxy, $C_6$–$C_{10}$ aryl, $C_7$–$C_{14}$ arylalkyl, $C_1$–$C_4$ haloalkyl, $C_3$–$C_7$ cycloalkyl, or alternately, $R^1$ and $R^2$ can be taken together with the carbon to which they are attached to form a 3–7 membered saturated carbocyclic ring system;

$R^{20}$ and $R^{21}$ are independently selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
$C_1$–$C_6$ alkylaminocarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$; or any group that, when administered to a mammalian subject, cleaves to form a free hydroxyl, amino or sulfhydryl;

$R^{11}$ is selected from one or more of the following:
H, keto, cyano, —CH$_2$N$R^{13}R^{14}$, —N$R^{13}R^{14}$, —O$R^{13}$, —S$R^{13}$, —S(O)$R^{13}$, —S(O)$_2R^{13}$, —N$R^{14}$C(=O)$R^{13}$, =NO$R^{14}$, —N$R^{14}$C(=O)O$R^{14}$, —OC(=O)N$R^{13}R^{14}$, —N$R^{13}$C(=O)N$R^{13}R^{14}$, —N$R^{14}$SO$_2$N$R^{13}R^{14}$, —N$R^{14}$SO$_2R^{13}$, —SO$_2$N$R^{13}R^{14}$, —OP(O)(O$R^{13}$)$_2$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, formyl, $C_3$–$C_6$ cycloalkoxy, $C_1$–$C_4$ alkyl substituted with —N$R^{13}R^{14}$, $C_1$–$C_4$ benzyloxyalkyl, methylenedioxy, ethylenedioxy, $C_1$–$C_4$ alkylcarbonyl, $C_1$–$C_4$ alkylcarbonylamino, 2-(1-morpholino)ethoxy, azido, or —C($R^{14}$)=N(O$R^{14}$);
1–3 amino acids linked together via amide bonds, said amino acid being linked via the amine or carboxylate terminus;
$C_3$–$C_{10}$ cycloalkyl substituted with 0–2 $R^{12}$;
$C_1$–$C_4$ alkyl substitued with 0–2 $R^{12}$
aryl($C_1$–$C_3$ alkyl)-, substituted with 0–2 $R^{12}$;
$C_2$–$C_6$ alkoxyalkyl-, substituted with 0–2 $R^{12}$;
$C_1$–$C_4$ alkylcarbonyloxy substituted with 0–2 $R^{12}$,
$C_6$–$C_{10}$ arylcarbonyloxy substituted with 0–2 $R^{12}$,
a $C_5$–$C_{14}$ carbocyclic residue substituted with 0–3 $R^{12}$;
a 5- to 10-membered heterocyclic ring system containing 1 to 4 heteroatoms independently selected from oxygen, nitrogen or sulfur, said heterocyclic ring system being substituted with 0–3 $R^{12}$;

$R^{114}$ is selected from one or more of the following:
H, keto, cyano, —CH$_2$N($R^{134}$)R$(^{144})$, —N($R^{134}$)R$(^{144})$, —CO$_2$H, —OC(=O)($C_1$–$C_3$ alkyl), —O-benzyl, $C_2$–$C_6$ alkoxyalkyl, —C(=O)NH$_2$, —OC(=O)NH$_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$alkylcarbonyl, $C_1$–$C_4$ alkylcarbonylamino, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system substituted with 0–3 $R^{12A}$.

$R^{12}$, when a substituent on carbon, is selected from one or more of the following:
phenyl, benzyl, phenethyl, phenoxy, benzyloxy, hydroxy, nitro, cyano, $C_1$–$C_4$ alkyl, $C_3$–$C_6$cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —O$R^{13}$, $C_1$–$C_4$ alkyl substituted with —N$R^{13}R^{14}$, —N$R^{13}R^{14}$, $C_2$–$C_6$ alkoxyalkylene optionally substituted with —Si(CH$_3$)$_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S$R^{13}$, —S(O)$R^{13}$, —S(O)$_2R^{13}$, —SO$_2$N$R^{13}R^{14}$, —NHSO$_2R^{14}$, —OCH$_2$CO$_2R^{13}$, 2-(1-morpholino)ethoxy, —C($R^{14}$)=N(O$R^{14}$); or
a 5- or 6-membered heterocyclic ring containing from 1 to 4 heteroatoms independently selected from oxygen, nitrogen or sulfur;
or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, hydroxy, or —N$R^{13}R^{14}$;
or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:
phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$N$R^{13}R^{14}$, —N$R^{13}R^{14}$, $C_2$–$C_6$ alkoxyalkyl, $C_1$–$C_4$ alkylcarbonyl, —C($R^{14}$)=N(O$R^{14}$);

$R^{12A}$, when a substituent on carbon, is selected from one or more of the following:
phenyl, benzyl, phenethyl, phenoxy, benzyloxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —O$R^{13}$, $C_2$–$C_6$ alkoxyalkyl optionally substituted with —Si(CH$_3$)$_3$, $C_1$–$C_4$ benzyloxyalkyl, methylenedioxy, ethylenedioxy, $C_1$–$C_4$ alkylcarbonyl, $C_1$–$C_4$ alkylcarbonylamino, —SMe, —S(O)Me, —S(O)$_2$Me, —OCH$_2$CO$_2R^{13}$, 2-(1-morpholino)ethoxy; or
a 5- or 6-membered heterocyclic ring containing from 1 to 4 heteroatoms independently selected from oxygen, nitrogen or sulfur;
or $R^{12A}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, benzyloxy; or, when $R^{12A}$ is attached to a saturated carbon atom, it may be =O or =S; or when $R^{12}$ is attached to sulfur it may be =O;

$R^{12A}$, when a substituent on nitrogen, is selected from one or more of the following:
  phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ alkylcarbonyl;

$R^{13}$ is selected from:
  phenyl substituted with 0–3 $R^{11A}$;
  benzyl substituted with 0–3 $R^{11A}$;
  $C_1$–$C_6$ alkyl substituted with 0–3 $R^{11A}$;
  $C_2$–$C_4$ alkenyl substituted with 0–3 $R^{11A}$;
  $C_1$–$C_6$ alkylcarbonyl substituted with 0–3 $R^{11A}$;
  $C_1$–$C_6$ alkoxycarbonyl substituted with 0–3 $R^{11A}$;
  $C_1$–$C_6$ alkylaminocarbonyl substituted with 0–3 $R^{11A}$;
  $C_3$–$C_6$ alkoxyalkyl substituted with 0–3 $R^{11A}$; an amine protecting group when $R^{13}$ is bonded to N;
  a hydroxy protecting group when $R^{13}$ is bonded to O;

$R^{14}$ is benzyloxy, $C_1$–$C_6$ alkyl substituted with 0–3 groups selected from —Obenzyl, $C_1$–$C_4$ alkoxy, $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{13A}$ and $R^{14A}$ are independently selected from: H, $C_1$–$C_6$ alkyl;

$R^{13A}$ and $R^{14A}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{15}$ is H or CH$_3$;

said method comprising the steps of:
(1) reacting an organodiol of formula (II):

(II)

wherein Q, m and n are defined as above, with a halogenating reagent in an aprotic organic solvent, preferably in a chlorinated organic solvent, with the proviso that the halogenating reagent is not a hydrogen halide, to form a compound of formula (IA);

(IA)

which is optionally isolated, where Q, X, m and n are defined as above; and (2) reacting compound (IA) with a reagent suitable for the protection of hydroxy groups to form the compound of formula (I) where $R^3$ is a hydroxy protecting group; and (3) reacting compound (IV) with compound (I) to form a compound of formula (V):

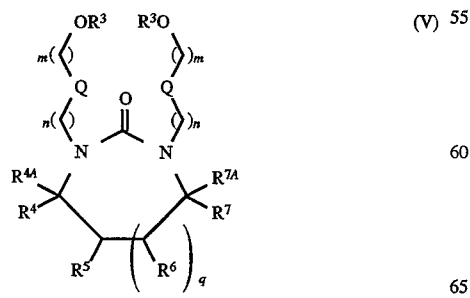
(V)

wherein $R^3$ is a hydroxy protecting group and $R^4$, $R^{4A}$, $R^5$, $R^6$, $R^7$ $R^{7A}$, m, n and q are as defined above.

Preferred in the present invention is the above method for alkylating compounds of the formula (IV) wherein:

q is 0, 1, or 2;

m and n are independently 1, 2 or 3;

X is chloro, bromo or iodo;

$R^3$ is hydrogen or a hydroxy protecting group;

$R^4$ and $R^7$ are independently selected from the following groups:
  hydrogen;
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$;

$R^{4A}$ and $R^{7A}$ are hydrogen;

$R^5$ is selected from fluorine, —N(R$^{20}$)$_2$, or —OR$^{20}$;

$R^6$ is independently selected from: hydrogen, fluorine, —OR$^{21}$;

$R^5$ and $R^6$ can alternatively join to form an epoxide or aziridine ring; —OCH$_2$SCH$_2$O—; —OCH$_2$O—; —OC(=S)O—; —OC(=O)C(=O)O—; —OC(R$^1$)(R$^2$)O—; —OC(OCH$_3$)(CH$_2$CH$_2$CH$_3$)O—; or any group that, when administered to a mammalian subject, cleaves to form a free dihydroxyl or diamino or hydroxyl and amino;

$R^1$ and $R^2$ are independently H, $C_1$–$C_4$ alkyl, or, alternately, $R^1$ and $R^2$ can be taken together with the carbon to which they are attached to form a 5–6 membered saturated carbocyclic ring system;

$R^{20}$ and $R^{21}$ are independently selected from:
  hydrogen;
  $C_1$–$C_6$ alkylcarbonyl substituted with 0–3 $R^{11}$;
  $C_1$–$C_6$ alkoxycarbonyl substituted with 0–3 $R^{11}$; benzoyl; or any group that, when administered to a mammalian subject, cleaves to form a free hydroxyl;

$R^{11}$ is selected from one or more of the following:
  H, keto, cyano, —CH$_2$NR$^{13}$R$^{14}$, —NR$^{13}$R$^{14}$, —OR$^{13}$, —S(O)$_p$R$^{13}$, $C_1$–$C_4$ alkyl, $C_2$–$C_4$ alkenyl, $C_3$–$C_{10}$ cycloalkyl substituted with 0–2 $R^{12}$, a $C_5$–$C_{14}$ carbocyclic residue substituted with 0–3 $R^{12}$, aryl ($C_1$–$C_3$ alkyl)-, substituted with 0–2 $R^{12}$, aryl substituted with 0–3 $R^{12}$; or
  a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$, when a substituent on carbon, is selected from one or more of the following:
  phenyl, benzyl, phenethyl, phenoxy, benzyloxy, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —OR$^{13}$, $C_1$–$C_4$ alkyl substituted with —NR$^{13}$R$^{14}$, —NR$^{13}$R$^{14}$, $C_2$–$C_6$ alkoxyalkylene optionally substituted with —Si(CH$_3$)$_3$, $C_1$–$C_4$ benzyloxyalkyl, methylenedioxy, ethylenedioxy, $C_1$–$C_4$alkoxycarbonyl, $C_1$–$C_4$ alkylcarbonyloxy, $C_1$–$C_4$ alkylcarbonyl, $C_1$–$C_4$ alkylcarbonylamino, —S(O)$_p$R$^{13}$, —SO$_2$NR$^{13}$R$^{14}$, —NHSO$_2$R$^{14}$, 2-(1-morpholino)ethoxy, —C(R$^{14}$)=N(OR$^{14}$); or
  a 5- or 6-membered heterocyclic ring containing from 1 to 4 heteroatoms independently selected from oxygen, nitrogen or sulfur;
  or $R^{12}$ may be a 3- or 4-carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$ alkoxy, hydroxy, or —$NR^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:
  phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkylcarbonyl, —$C(R^{14})=N(OR^{14})$;

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

$R^{15}$ is H or $CH_3$;

p is 0, 1 or 2;

Q is independently selected at each occurrence from the following:
  $C_1$–$C_8$ alkyl substituted with 0–3 $R^{31}$;
  $C_2$–$C_8$ alkenyl substituted with 0–3 $R^{31}$;
  $C_2$–$C_8$ alkynyl substituted with 0–3 $R^{31}$;
  a $C_3$–$C_{14}$ carbocyclic ring system substituted with 0–5 $R^{31}$ or 0–5 $R^{32}$;

$R^{31}$ is selected from one or more of the following:
  cyano, —$CH_2NR^{13}R^{14}$, —$NR^{13}R^{14}$, —$OR^{13}$, $C_2$–$C_6$ alkoxyalkyl, —$S(O)_pR^{13}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, formyl, $C_3$–$C_6$ cycloalkoxy, $C_1$–$C_4$ alkyl substituted with —$NR^{13}R^{14}$, $C_1$–$C_4$ alkoxycarbonyl, $C_1$–$C_4$ alkylcarbonyloxy, $C_1$–$C_4$ alkylcarbonyl, —$OCH_2CO_2R^{13}$, 2-(1-morpholino)ethoxy, azido, —$C(R^{14})=N(OR^{14})$; or
  a $C_5$–$C_{14}$ carbocyclic residue substituted with 0–5 $R^{32}$; or
  aryl substituted with 0–3 $R^{32}$; or
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
  phenethyl, phenoxy, $C_3$–$C_{10}$ cycloalkyl, $C_3$–$C_6$ cycloalkylmethyl, $C_7$–$C_{10}$ arylalkyl, benzyl protected oxime, $C_2$–$C_6$ alkoxyalkyl, methylenedioxy, ethylenedioxy, $C_1$–$C_4$ alkylcarbonyloxy, —$NHSO_2R^{14}$, benzyloxy, 2-(1-morpholino)ethoxy, —$CONR^{13}NR^{13}R^{14}$, cyano, sulfonamide, $C_3$–$C_6$ cycloalkoxy, —$NR^{13}R^{14}$, —$C(R^{14})=N(OR^{14})$, —$NO_2$, —$OR^{13}$, —$NR^{40}R^{41}$, —$SO_pR^{13}$, —$SO_pNR^{13}R^{14}$, —$C(=O)NR^{13}R^{14}$, —$OC(=O)NR^{13}R^{14}$, —$C(=O)R^{11}$, phenyl, —$C(=O)NR^{13}$-($C_1$–$C_4$ alkyl)-$NR^{13}R^{14}$, 13 $C(=O)NR^{40}R^{41}$, —$C(=O)NR^{13}C(R^{11})_2NR^{13}R^{14}$;
  —$C(=O)NR^{13}C(R^{11})_2NR^{13}CO_2R^{13}$;
  —$C(=O)NR^{13}$-($C_1$–$C_4$ alkyl)-$NR^{13}CO_2R^{13}$;
  —$C(=O)N(R^{13})$-($C_1$–$C_4$ alkyl)-$R^{11}$; or
  —$C(=O)C(R^{11})_2NR^{13}R^{14}$;
  —$C(=O)C(R^{11})_2NR^{13}CO_2R^{13}$; —$C(=O)$-($C_1$–$C_4$ alkyl)-$NR^{13}R^{14}$; —$C(=O)$-($C_1$–$C_4$ alkyl)-$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or benzyloxy;

$C_1$–$C_4$ alkyl substituted with 0–4 groups selected from: $R^{11}$, =$NR^{14}$, =$NNR^{13}C(=O)NR^{13}R^{14}$, or —$NR^{13}R^{14}$;

$C_2$–$C_4$ alkenyl substituted with 0–4 $R^{11}$;

$C_2$–$C_4$ alkynyl substituted with 0–4 $R^{11}$;

a 5- or 6-membered heterocyclic ring containing from 1 to 4 heteroatoms independently selected from oxygen, nitrogen or sulfur, substituted with 0–2 $R^{12}$;

or $R^{32}$ may be a 3- or 4- carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, benzyloxy, or —$NR^{13}R^{14}$; or, when $R^{32}$ is attached to a saturated carbon atom, it may be =O, =S, =NO-benzyl; or when $R^{32}$ attached to sulfur it may be =O;

$R^{40}$ is selected from: H, $C_1$–$C_3$ alkyl;

$R^{41}$ is selected from:
  —$C(=O)NR^{13}R^{14}$;
  —$C(=O)NR^{13}NR^{13}R^{14}$;
  —$C(=O)C(R^{11})_2NR^{13}R^{14}$;
  —$C(=O)C(R^{11})_2NR^{13}NR^{13}R^{14}$;
  —$C(=O)C(R^{11})_2NR^{13}CO_2R^{13}$;
  —$C(=O)H$;
  —$C(=O)R^{11}$;
  —$C(=O)$-($C_1$–$C_4$ alkyl)-$NR^{13}R^{14}$;
  —$C(=O)$-($C_1$–$C_4$ alkyl)-$NR^{13}CO_2R^{13}$;
  1–3 amino acids linked together via amide bonds, and linked to the N atom via the carboxylate terminus;

More preferred in the present invention is the above method for alkylating compounds of the formula (IV) wherein:

q is 1;

m and n are independently 1, 2 or 3;

X is chloro, bromo or iodo;

$R^3$ is a hydroxy protecting group;

$R^4$ and $R^7$ are independently selected from: benzyl, fluorobenzyl, pyrrolylmethyl, methoxybenzyl, isobutyl, nitrobenzyl, N-protected aminobenzyl, thienylmethyl, O-protected hydroxybenzyl, pyridylmethyl, or naphthylmethyl;

$R^{4A}$ and $R^{7A}$ are hydrogen;

$R^5$ is —$OR^{20}$;

$R^6$ is —$OR^{21}$;

$R^5$ and $R^6$ can alternatively join to form an —$OCH_2SCH_2O$—; —$OCH_2O$—; —$OC(=S)O$—; —$OC(=O)C(=O)O$—; —$OC(CH_3)_2O$—; —$OC(OCH_3)(CH_2CH_3)O$—; or any group that, when administered to a mammalian subject, cleaves to form a free dihydroxyl or hydroxyl;

$R^{20}$ and $R^{21}$ are independently selected from:
  hydrogen;
  $C_1$–$C_6$ alkylcarbonyl substituted with 0–3 $R^{11}$;
  $C_1$–$C_6$ alkoxycarbonyl substituted with 0–3 $R^{11}$; benzoyl; or any group that, when administered to a mammalian subject, cleaves to form a free hydroxyl, $R^{11}$ is selected from one or more of the following:
  H, keto, cyano —$CH_2NR^{13}R^{14}$, —$NR^{13}R^{14}$, —$OR^{13}$, —$S(O)_pR^{13}$, $C_1$–$C_4$ alkyl, $C_2$–$C_4$ alkenyl, $C_3$–$C_{10}$ cycloalkyl substituted with 0–2 $R^{12}$, a $C_5$–$C_{14}$ carbocyclic residue substituted with 0–3 $R^{12}$, aryl ($C_1$–$C_3$ alkyl)-, substituted with 0–2 $R^{12}$, aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$ when a substituent on carbon, is selected from one or more of the following:

phenyl, benzyl, phenethyl, phenoxy, benzyloxy, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_pR^{13}$, —$SO_2NR^{13}R^{14}$, —$NHSO_2R^{14}$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6-membered ring being optionally substituted on the aliphatic carbons with $C_1$–$C_4$ alkyl, $C_1$–$C_4$alkoxy, hydroxy, or —$NR^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkylcarbonyl, —$C(R^{14})=N(OR^{14})$;

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

$R^{15}$ is H or $CH_3$;

p is 0, 1 or 2;

Q is independently selected at each occurrence from the following:

allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, phenyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorophenyl, quinolinylmethyl, carboxyphenyl, benzyloxyphenyl, phenylphenyl, adamantylethyl, cyclopropylmethoxyphenyl, methoxyphenyl, methylphenyl, ethoxyphenyl, benzyloxyphenyl, benzyloxymethylphenyl, N-protected aminophenyl, formylphenyl, cyanophenyl, cinnamyl, allyloxyphenyl, fluorophenyl, difluorophenyl, fluoromethylphenyl, cyclobutylmethyl, cyclopentylmethyl, nitrophenyl, ($H_2NC(=O)$)-phenyl, carbomethoxyphenyl, carboethoxyphenyl, tetrazolylphenyl, and dimethylallyl, N-protected aminomethylphenyl, (O-benzyl-formaldoxime)phenyl, (O-methyl-formaldoxime)phenyl, ($CH_3O_2CO$)-phenyl, (benzyl-$OCH_2CH_2N=CH$)-phenyl, N-benzylaminocarbonylphenyl, N-protected N-methylaminophenyl, N-protected N-ethylaminophenyl, N-protected N-ethylaminomethylphenyl, acetylphenyl, acetoxyphenyl, N-benzyloxylaminophenyl, N-benzyloxylaminomethylphenyl, (benzyloxy)ethylphenyl, ($CH_3C(=NO$-benzyl))-phenyl, ($H_2NNHC(=O)$)-phenyl, ($H_2NC(=O)NHN=CH$)-phenyl, ($CH_3ONHC(=O)$)-phenyl, ($HONHC(=O)$)- phenyl, ($CH_3NHC(=O)$)-phenyl, N,N-dimethylaminocarbonylphenyl, (benzyl-$OCH_2CH(OH)CH_2O$)-phenyl, benzyloxyethoxybenzyl (oxazolidinyl)-phenyl, (benzyloxyl)hexyl, hexenyl, (benzyloxy)octyl, (benzyloxyl)pentyl, (carboxy)pentyl, (carbomethoxy)pentyl, (methylthio)phenyl, (methylsulfonyl)phenyl, N,N-dimethylaminomethylphenyl, N-protected N-methylaminomethylphenyl, glycylaminophenyl, N,N-dimethylglycylaminophenyl, alanylaminophenyl, (N-phenylmethoxycarbonyl) alanylaminophenyl, phenylalanylaminophenyl, (N-phenylmethoxycarbonyl) phenylalanylaminophenyl, ($CH_3CH_2NHC(=O)$)-phenyl, N,N-diethylaminocarbonylphenyl, N-ethylaminocarbonylphenyl, N-propylaminocarbonylphenyl, N,N-diisopropylaminocarbonylphenyl, N,N-di-n-propylaminocarbonylphenyl, (benzyloxypropynyl) phenyl, (imidazolyl—$C(=O)$)-phenyl, (pyrazolyl-C($=O$))-phenyl, (pyridylmethylaminocarbonyl) phenyl, (oxadiazolidinonyl)phenyl, trifluoroacetylphenyl, (pyrazolyl)phenyl, ($H_2NSO_2$) -phenyl, dibenzyloxyethylphenyl, (MeHNC($=O$)NH)-phenyl, ($H_2NC(=O)NH$)-phenyl, ($HC(=O)NH$)-phenyl, methanesulfonylpentyl, methoxypentyl, N-formyl-N-methylaminophenyl, acetylaminophenyl, propionylphenyl, butyrylphenyl, ($CH_3CH_2C(=NObenzyl)$)-phenyl, (trifluorohydroxyethyl)phenyl, ($CF_3C(=NOH)$)-phenyl, (N-methylglycyl)aminophenyl, ((4-morpholino)ethyl)aminocarbonylphenyl, (N,N-dimethylaminoethyl)aminocarbonylphenyl, (N,N-diethylaminoethyl)aminocarbonylphenyl, (4-methylpiperazin-1-ylethyl)aminocarbonylphenyl, (benzyl-NHC($=O$)O)phenyl, ($CH_3NHC(=O)O$) phenyl, ($NH_2C(=O)CH_2O$)phenyl, ($NH_2C(=NH)$) phenyl, ((N-phenylmethoxycarbonyl)glycylamino) phenyl, (imidazolylmethyl)phenyl, (($CH_3)_3C$—C($=O$))phenyl, (N-methyl-N-ethylaminoethyl) aminocarbonylphenyl, (pyrrolidinylethyl) aminocarbonylphenyl, (piperidinylethyl) aminocarbonylphenyl, ($H_2NC(=NObenzyl)$) phenyl, ($H_2NC(=NObenzyl)$)fluorophenyl, benzimidazolylmethyl, benzotriazolylmethyl, indazolylmethyl, benzoxazolinylmethyl, benzisoxazolylmethyl, thienylmethyl, or furylmethyl.

Further preferred in the present invention is the above method for alkylating compounds of formula (IV) wherein:

q is 1;

m and n are independently 1, 2 or 3;

X is chloro, bromo or iodo;

$R^3$ is a hydroxy protecting group;

$R^4$ and $R^7$ are independently selected from:

benzyl, fluorobenzyl, pyrrolylmethyl, methoxybenzyl, isobutyl, nitrobenzyl, N-protected aminobenzyl, thienylmethyl, O-protected hydroxybenzyl, pyridylmethyl, or naphthylmethyl;

$R^{4A}$ and $R^{7A}$ are hydrogen;

$R^5$ and $R^6$ join to form —OC(CH$_3$)$_2$O—;

Q is independently selected at each occurrence from the following:

allyl, propyl, cyclopropylmethyl, n-hexyl, n-butyl, CH$_2$CH=C(CH$_3$)$_2$, methallyl, i-pentyl, phenyl, hexyl, isoprenyl, cinnamyl, fluorophenyl, (methylsulfonyl)phenyl, cyclopropylmethyl, naphthylmethyl, 4-pyridinylmethyl, benzyloxyhexyl, 2-pyridinylmethyl, carboxypentyl, cyclopentylmethyl, cyanophenyl, quinolinylmethyl, vinylphenyl, benzyloxyphenyl, benzyloxyphenyl, benzyloxypentyl, (benzyloxyl)methylphenyl, carbomethoxyphenyl, formylphenyl, (O-benzyl-formaldoxime)phenyl, cyclobutylmethyl, difluorophenyl, nitrophenyl, N-protected aminomethylphenyl, 3-(NHCHO)phenyl, dibenzyloxyphenyl, N-benzyloxylaminomethylphenyl, 3-(CH$_3$OC(=O)O-phenyl, 3-(1-benzyloxyethyl)phenyl, 3-(HOCH$_2$CH$_2$N=CH)phenyl, 3-(2-oxazolidinyl)phenyl, 3-(C$_6$H$_5$CH$_2$NHC(=O)O)phenyl, 3-(CH$_3$NHC(=O)O)phenyl, acetylphenyl, (CH$_3$C(=NO-benzyl))-phenyl, 2-(hydroxymethyl)-cyclopropylmethyl, (H$_2$NNHC(=O))-phenyl, (H$_2$NC(=O)NHN=CH)-phenyl, 3-[(N-methoxy)aminocarbonyl]-phenyl, 4-[(N-methoxy)aminocarbonyl]-phenyl, benzyloxyethoxyphenyl, (benzyl-OCH$_2$CH (Obenzyl)CH$_2$O)-phenyl, (NH$_2$C(=NH))phenyl, (methylaminocarbonyl)phenyl, 3-formyl-4-benzyloxyphenyl, 3-(1,2-dibenzyloxyethyl)phenyl, (methylaminocarbonyl)phenyl, (H$_2$NC(=O)NH)-phenyl, N-protected N-methylaminophenyl, N-protected aminophenyl, N,N-dimethylaminophenyl, 3-propionylphenyl, (CH$_3$NHC(=O)NH)-phenyl, 3-(2-imidazolyl—C(=O))phenyl, 3-(CH$_3$CH$_2$C(=N-Obenzyl))phenyl, N,N-dimethylglycylaminophenyl, 3-((N-phenylmethoxycarbonylaminoglycyl)amino)phenyl, 3-( (N-phenylmethoxycarbonylamino-L-alanyl) amino)phenyl, 3-((N-phenylmethoxycarbonylamino-L-phenylalanyl) amino)phenyl, 3-(CF$_3$CH$_2$C(=N-Obenzyl))phenyl, alanylaminophenyl, phenylalanylaminophenyl, (methylsulfonyl)pentyl, N-protected N-ethylaminocarbonylphenyl, 3-(N-imidazolylmethyl)phenyl, 3-(2,2,2-trifluoro-1-hydroxyethyl)phenyl, N-diethylaminocarbonylphenyl, N-protected N-propylaminocarbonylphenyl, pyridinylmethyl, aminocarbonylphenyl, 3-(H$_2$NC(=NObenzyl)-4-fluorophenyl, 3-(5-methyl-1,2,3-oxadiazolyl)phenyl, 3-(H$_2$NC(=NObenzyl)-4-fluorophenyl, benzimidazolylmethyl, benzotriazolylmethyl, indazolylmethyl, N-protected 3-ethylamino-5-indazolylmethyl, or 3-amino-5-benzisoxazolylmethyl.

Preferred in the present invention is the above method wherein q=1 and $R^5$ and $R^6$ are taken together to form —OC(CH$_3$)$_2$O—.

Also preferred in the present invention is a process for alkylating a cylic urea compound of formula (IVb):

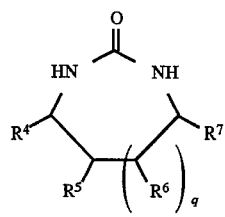

wherein:

$R^4$ and $R^7$ are independently benzyl, fluorobenzyl, pyrrolylmethyl, methoxybenzyl, isobutyl, nitrobenzyl or aminobenzyl;

$R^5$ and $R^6$ are independently hydrogen or —OR;

R is a hydroxy protecting group; and q is 0, 1 or 2;

comprising the steps of:

(1) reacting an organodiol of formula (IIb):

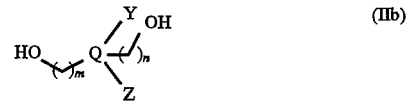

wherein Q, Y, Z, m and n are defined as above, with a halogenating reagent in a chlorinated organic solvent, with the proviso that the halogenating reagent is not a hydrogen halide, to form a compound of formula (IAb);

where Q, X, Y, Z, m and n are defined as above;

(2) reacting compound (IAb) with a reagent suitable for the protection of hydroxy groups to form the compound of formula (Ib) where $R^3$ is a hydroxy protecting group; and (3) reacting compound (IVb) with compound (Ib) to form a compound of formula (Vb):

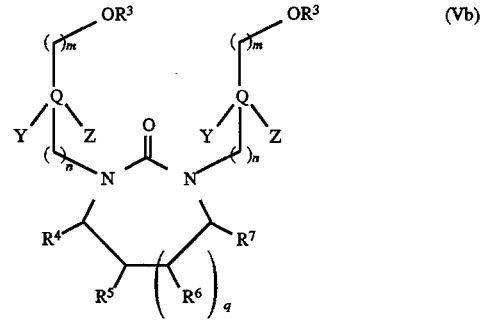

wherein $R^3$ is a hydroxy protecting group and $R^4$, $R^5$, $R^6$, $R^7$ Q, Y, Z m, n and q are as defined above The method of the present invention is useful for preparing hydroxy halide and organooxy halide alkylating agents by reacting an organodiol compound and a halogenating reagent in a chlorinated organic solvent. The halogenating reagent is not a hydrogen halide. In general, the synthetic methods of the present invention are more efficient, cost-effective and provide higher yields than those of the prior art.

The processes of the present invention are useful for the preparation of cyclic HIV protease inhibitors, including cyclic urea HIV protease inhibitors, and for the synthesis of compounds useful as intermediates for the synthesis of such cyclic protease inhibitors. Such cyclic HIV protease inhibitors are useful for the inhibition of HIV and the treatment of HIV infection. Such cyclic HIV protease inhibitors are also useful for the inhibition of HIV in an ex vivo sample containing HIV or expected to be exposed to HIV. Thus, such cyclic HIV protease inhibitors may be used to inhibit HIV present in a body fluid sample (for example, a serum or semen sample) which contains or is suspected to contain or be exposed to HIV. Such cyclic HIV protease inhibitors are also useful as standard or reference compounds for use in tests or assays for determining the ability of an agent to inhibit viral replication and/or HIV protease, for example in a pharmaceutical research program. Thus, such cyclic HIV protease inhibitors may be used as a control or reference compound in such assays and as a quality control standard. Such cyclic HIV protease inhibitors may be provided in a commercial kit or container for use as such standard or reference compound. Since such cyclic HIV protease inhibitors exhibit specificity for HIV protease, they may also be useful as diagnostic reagents in diagnostic assays for the detection of HIV protease. Thus, inhibition of the protease activity in an assay by such a cyclic HIV protease inhibitor would be indicative of the presence of HIV protease and HIV virus.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures ranging from the solvent's freezing temperature to the solvent's boiling temperature. Depending on the particular reaction step, suitable solvents for a particular reaction step may be selected and may include aprotic solvents, including but not limited to polar aprotic organic solvents. Depending on the particular reaction step, suitable solvents for a particular reaction step may be selected and may include, but are not limited to, toluene, pyridine, dimethylsulfoxide (DMSO), N,N-dimethylformamide (DMF), N,N-dimethylacetamide (DMAC), diethyl ether, benzene, or tetrahydrofuran (THF). Suitable solvents may include chlorinated organic solvents which include, but are not limited to, chloroform, methylene chloride, tetrachloroethane, butyl chloride and dichloroethane. Suitable non-chlorinated organic solvents may include, but are not limited to tetrahydrofuran (THF), diethyl ether and toluene.

As used herein, by "halogenating reagent" it is meant any reagent or combination of reagents which can effect the conversion of a hydroxy alkyl group to a halo alkyl group. The halo group is preferably chloro, bromo, or iodo. Such halogenating reagents may include, but are not limited to, thionyl halides, such as thionyl chloride and thionyl bromide; oxalyl halides, such as oxalyl chloride and oxalyl bromide; phosphorous pentahalides, such as phosphorous pentachloride and phosphorous pentabromide; phosphorous oxychloride and iodination reagents such as methyltrichlorosilane/sodium iodide and phosphorus triiodide.

By "reagent suitable for the protection of hydroxy groups" it is meant any reagent or combination of reagents which can effect the protection of a hydroxy group with a hydroxy protecting group.

As used herein, the term "hydroxy protecting group" (or "O-protected") refers to any group known in the art of organic synthesis for the protection of hydroxy groups. Such protecting groups include those listed in Greene and Wuts, "Protective Groups in Organic Synthesis", John Wiley & Sons, New York (1991), the disclosure of which is hereby incorporated by reference. The hydroxy protecting groups are preferably base-stable and can include, but are not limited to acyl types, aromatic carbamate types and alkyl types. Exemplary are methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxy protecting groups may include the following protecting groups as ethers: tetrahydropyranyl, triphenylmethyl, benzyl, tetrahydrofuranyl, allyl, methoxymethyl (MOM), benzyloxymethyl, p-methoxybenzyloxymethyl, 2-trimethylsilylethoxymethyl (SEM), t-butoxymethyl, methylthiomethyl, 2-methoxyethoxymethyl, trichloroethoxymethyl, t-butyl, p-methoxybenzyl, t-butyldimethylsilyl, o-nitrobenzyl, p-methoxyphenyldiphenylmethyl, p-nitrobenzyl, triisopropylsilyl, t-butyldiphenylsilyl.

The preferred conditions to remove tetrahydropyranyl, triphenylmethyl, tetrahydrofuranyl, methoxymethyl, benzyloxymethyl, p-methoxybenzyloxymethyl, 2-trimethylsilylethoxymethyl, t-butoxymethyl, methylthiomethyl, 2-methoxyethoxymethyl, trichloroethoxymethyl, t-butyl, p-methoxyphenyldiphenylmethyl, are: (a) 1–4M HCl in anhydrous or aqueous methanol, ethanol, isopropanol, tetrahydrofuran, dioxane, or diethyl ether; (b) 1–4M H2SO4 in anhydrous or aqueous methanol, ethanol, isopropanol, tetrahydrofuran, dioxane, or diethyl ether; (c) polystyrene sulfonic acid resin in anhydrous or aqueous methanol, ethanol, isopropanol, tetrahydrofuran, dioxane, or diethyl ether; (d) 10–100% trifluoroacetic acid in dichloromethane; or(e) p-toluenesulfonic acid or camphorsulfonic acid in anhydrous or aqueous methanol, ethanol, isopropanol.

The preferred conditions to remove benzyl, benzyloxymethyl, p-methoxybenzyloxymethyl, p-methoxybenzyl, o-nitrobenzyl, p-nitrobenzyl are: hydrogenolysis in the presence of 1–17% palladium on carbon, or palladium black. Also preferred conditions to remove o-nitrobenzyl group is to irradiate the compound at 320 nm wavelength for 5–60 minutes.

The preferred conditions to remove 2-trimethylsilylethoxymethyl, t-butyldimethylsilyl, triisopropylsilyl, t-butyldiphenylsilyl are: treatment of the compound with tetrabutylammonium fluoride; or hydrogen flouride pyridine complex in THF, DMF or dimethylpropyleneurea.

The preferred conditions to remove allyl is: isomerization of the allyl ether with [Ir(COD)(Ph$_2$MeP)$_2$]PF$_6$ or (Ph$_3$P)$_3$RhCl in tetrahydrofuran, diethyl ether or dioxane followed by hydrolysis with aqueous HgCl$_2$.

All Of the above mentioned deprotection reactions can be carried out at temperetaures ranging from 0 degree C to a solvent reflux.

As used herein, the term "cyclic acetal protecting group" includes any protecting group known in the art of organic synthesis for the protection of 1,2-diol group through formation of a cyclic acetal. Such protecting groups include, but are not limited to, those listed in Greene and Wuts, "Protective Groups in Organic Synthesis", John Wiley & Sons, New York (1991), the disclosure of which is hereby incorporated by reference. Examples of such cyclic acetal 1,2-diol protecting groups are methylene acetal, ethylidene acetal, 2,2,2-trichloroethylidene acetal, acetonide, cycloheptylidene ketal, cyclopentylidene ketal, cyclohexylidene ketal, benzylidene acetal, phenanthrylidene, and methoxymethylene acetal.

As used herein, the term "amine protecting group" (or "N-protected") refers to any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert- butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetrahydrothio-xanthyl)]methyl carbamate; 2-trimethylsilylethyl carbamate; 2-phenylethyl carbamate; 1,1-dimethyl-2,2-dibromoethyl carbamate; 1-methyl-1(4-biphenylyl)ethyl carbamate; benzyl carbamate; p-nitrobenzyl carbamate; 2-(p-toluenesulfonyl)ethyl carbamate; m-chloro-p-acyloxybenzyl carbamate; 5-benzyisoxazolylmethyl carbamate; p-(dihydroxyboryl) benzyl carbamate; m-nitrophenyl carbamate; o-nitrobenzyl carbamate; 3,5-dimethoxybenzyl carbamate; 3,4-dimethoxy-6-nitrobenzyl carbamate; N'-p-toluenesulfonylaminocarbonyl; t-amyl carbamate; p-decyloxybenzyl carbamate; diisopropylmethyl carbamate; 2,2-dimethoxycarbonylvinyl carbamate; di(2-pyridyl) methyl carbamate; 2-furanylmethyl carbamate; phthalimide; dithiasuccinimide; 2,5-dimethylpyrrole; benzyl; 5-dibenzylsuberyl; triphenylmethyl; benzylidene; diphenylmethylene; or methanesulfonamide.

The compounds herein described may have asymmetric centers. Unless otherwise indicated, all chiral, diastereomeric and racemic forms are included in the present invention. Geometric isomers of C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, Q, $R^3$, $R^6$, $R^{31}$, $R^{32}$, $R^{13}$, $R^{14}$, $R^{11}$, $R^{11A}$, $R^{12}$, $R^{12A}$, m, and n) occurs more than one time in any constituent or in any formula, its definition on each occurrence is independent of its definition at every other occurrence. Thus, for example, if a group is shown to be substituted with 0–2 $R^{11}$, then said group may optionally be substituted with up to two $R^{11}$ and $R^{11}$ at each occurrence is selected independently from the defined list of possible $R^{11}$.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —CvFw where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

In the definition of Q, the Q group is bonded to the rest of the molecule of formulas (I), (II), (IA), or (V) by two bonds attaching to the same or any two different carbon atoms in the Q group.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl) aryl" is intended to refer to a $C_1$–$C_3$ alkyl group which is attached through an aryl ring to the residue of the indicated compound; the term "aryl(C₁–C₃ alkyl)" is intended to refer to an aryl group attached through a C₁–C₃ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridinyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenarsazinyl, phenothiazlnyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzlsoxazolyl, oxindolyl, benzoxazolinyl, or isatinoyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) The Peptides, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The method of the invention comprises the following steps as described further below.

Step (1):

Step (1) (the halogenation step) comprises reacting an organodiol compound of the formula

with a halogenating reagent. The halo group is preferably chloro, bromo, or iodo. Such halogenating reagents may include, but are not limited to, thionyl halides, such as thionyl chloride and thionyl bromide; oxalyl halides, such as oxalyl chloride and oxalyl bromide; phosphorous pentahalides, such as phosphorous pentachloride and phosphorous pentabromide; phosphorous oxychloride; and iodination reagents. Preferably, the halogenating reagent is thionyl chloride.

The halogenation reaction step (1) is conducted in a suitable aprotic solvent, preferably a chlorinated organic solvent. Such chlorinated organic solvents useful in the method of the invention may include, but are not limited to, chloroform, methylene chloride, tetrachloroethane, butyl chloride and dichloroethane. Preferably, the chlorinated organic solvent is selected from chloroform or methylene chloride.

The halogenation reaction can be conducted at a temperature of from about −40° C. to about the boiling point of the reaction solvent selected, 61° C. in the case of chloroform. Preferably, the temperature of the reaction is about 0° C. to about room temperature.

The time required for completion of the reaction may range from about 1 hour to about 5 days, depending on the combination of halogenating reagent, solvent and regioisomer of compound (II) selected. The reaction can be run under nitrogen or in the presence of slightly humid air, provided that any changes in concentration and integrity of the reagents due to decomposition are compensated for.

The product of the reaction step (1) of compound (II) with a halogenating reagent is a hydroxy halide alkylating agent having a formula:

Step (2).

Organooxy halide alkylating agents of formula (I) where R³ is a hydroxy protecting group are prepared by reacting the compound of formula (IA) with a reagent suitable for the protection of hydroxy groups (also referred to herein as a hydroxy protecting group reagent) to provide an $R^3$ hydroxy protecting group whose incorporation in formula (IA) will serve to protect the hydroxyl functionality. Such protecting groups include those listed in Greene and Wuts, "Protective Groups in Organic Synthesis", John Wiley & Sons, New York (1991), the disclosure of which is hereby incorporated by reference. The hydroxy protecting groups are base-stable and can include, but are not limited to acyl types, aromatic carbamate types and alkyl types. Exemplary are methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

A preferred hydroxy protecting group is triphenylmethyl since it facilitates the isolation of compounds (I) and (V) in high purity, without the use of chromatography.

Reaction conditions used for incorporation of the hydroxy protecting groups can also be found in the Greene and Wuts reference cited above. These reaction conditions may be modified to include other combinations of reagents, such as dimethylacetamide as solvent, use of acid scavengers such as Hunig's base (N,N-diisopropylethylamine), and use of less than one equivalent of hydroxy protecting group reagent to optimize yield of the products.

The possible undesired reaction of the hydroxy protecting group reagent containing the $R^3$ hydroxy protecting group with X under basic conditions may lead to the formation of undesired by-products. Acid catalyzed protection of an alcohol is a reversible reaction and in the case of triphenylmethylation, can lead to aldehyde formation as reported by Smith and Smith, J. Am. Chem. Soc., 70, 2400–2401 (1948). It has been found in the present invention that HCl catalysis gives good yields of the compound of formula (I) where $R^3$ is triphenylmethyl, when the hydroxy protecting group reagent is triphenylmethyl chloride, triphenylmethyl alcohol, or triphenylmethyl methyl ether. The preferred hydroxy protecting group reagent source for the triphenylmethyl hydroxy protecting group are triphenylmethyl methyl ether or triphenylmethyl alcohol, since azeotropic removal of methanol or water, respectively, drive the triphenylmethylation reaction to completion.

The compound of formula (I) may preferably be prepared by carrying out steps (1) and (2) of the present process without the isolation (for example, without isolation by chromatographic separation or precipitation) of the intermediate compound of formula (IA). Eliminating the need for isolating the intermediate compound of formula (IA) results in an overall increase in the yield of the desired compound of formula (I) in the process of the present invention. Thus, the process of the present invention may be carried out using a "one pot procedure" wherein steps (1) and (2) of the process of the present invention are carried out in one reaction vessel without isolation of compound (IA) between the two steps.

A reaction scheme representative of the methods of the invention for preparing hydroxy halide or organooxy halide alkylating agents is shown in the following Scheme 1.

SCHEME 1

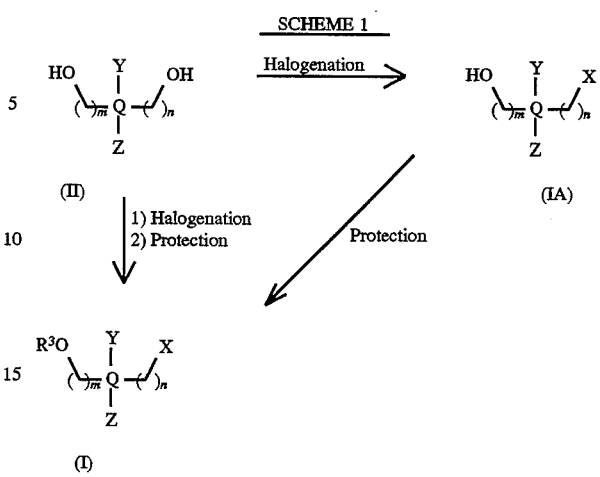

Step (3).

The present invention includes a process useful for alkylating cyclic urea compounds of formula (IV):

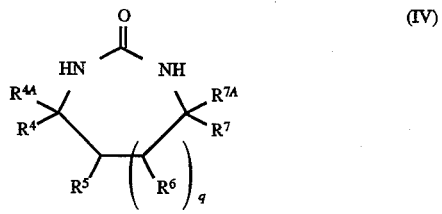

which comprises reacting a cyclic urea compound of formula (IV) with a hydroxy-protected compound of formula (I) in the presence of a suitable base. Such suitable bases to provide basic conditions can include, but are not limited to, metal hydrides in non-protic solvents, such as, but not limited to, tetrahydrofuran, ether, N,N-dimethylformamide or 1,3-dimethyl-3,4,5,6-tetrahydro-2(1H)-pyrimidinone (DMPU); a strong metal hydroxide under phase-transfer conditions, such as, but not limited to, water/toluene; or strong metal alkoxides or disilazides in an ethereal solvent, such as, but not limited to, tetrahydrofuran or ether. A preferred base in step (3) is potassium t-butoxide or potassium bis(trimethylsilyl)amide in THF. The method yields reaction products of formula (V):

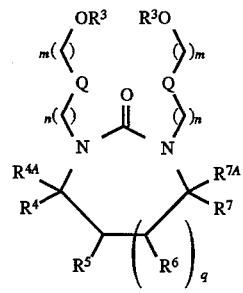

wherein $R^3$ is a hydroxy protecting group. Compounds of formula (V) can be reacted with acid to remove the hydroxy protecting group $R^3$ (i.e., can be acid-deprotected, substituting $R^3$ with H) to yield compounds useful as inhibitors of HIV protease and for the treatment of HIV infection and disease.

Scheme 2 represents the method for alkylating cyclic urea compounds of formula (IV).

SCHEME 2

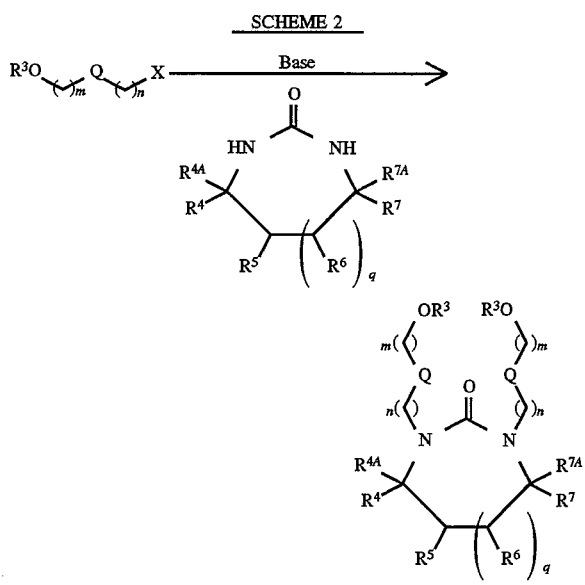

In the present invention it is preferred that:

q is 1;

$R^4$ and $R^7$ are benzyl;

$R^5$ and $R^6$ are taken together to form —OC(CH$_3$)$_2$O— (acetonide blocked diol).

When $R^5$ and $R^6$ are taken together to form —OC(CH$_3$)$_2$O— the alkylation reaction rate is increased. Also, when $R^5$ and $R^6$ are taken together to form —OC(CH$_3$)$_2$O—, the product from reaction with 4-(triphenylmethoxymethyl) benzyl chloride is crystalline and easily purifiable.

The present invention is further described below with reference to the following specific, non-limiting Examples.

EXAMPLES

All chemicals and solvents were reagent grade and were used as supplied without further purification. Chloroform and thionyl chloride may be obtained from Baker. Thin layer chromatography (TLC) may be performed on Silica Gel 60 F$_{254}$ TLC plates (layer thickness 0.2 mm) from EM Separations. TLC visualization was accomplished using UV light, iodine, 5% phosphomolybdic acid in ethanol and/or ninhydrin spray. Melting points were determined using a Thomas Hoover or Electrothermal 9200 melting point apparatus and are uncorrected. NMR spectra were recorded on a 300 MHz General Electric QE-300, Varian 300, or Varian 400 spectrometer.

Examples 1 and 2 demonstrate methods for the preparation of compounds of the formula (I) where $R^3$ is hydrogen. Examples 3–8 demonstrate the preparation methods of formula (I) compounds where $R^3$ is a hydroxy protecting group. Examples 9 and 10 demonstrate the alkylation of cyclic urea nitrogens by the compounds of formula (I).

EXAMPLE 1 p-Hydroxymethylbenzyl chloride 1,4-benzenedimethanol (13.8 g, 0.10 mole) was dispersed in chloroform (100 mL) in a 500 mL three-neck round bottom flask equipped with a magnetic stirring bar, an addition funnel, a nitrogen inlet and a gas scrubber. The mixture was cooled to 0° C. in an ice bath. Thionyl chloride (13.1 g, 0.11 mole) dissolved in chloroform (10 mL) was added dropwise over ten minutes with rapid stirring to the cooled mixture. As the addition proceeded, the mixture largely cleared. During the addition step, and for one hour thereafter, the reaction flask was swept with nitrogen which was then passed through the scrubber before venting to the atmosphere. The nitrogen was turned off and the scrubber disconnected. The mixture was allowed to come to room temperature and stirring was continued for 20 hours. Sufficient sodium bicarbonate was added to neutralize any residual hydrogen chloride. The mixture was filtered through a coarse glass frit and the solvent removed under reduced pressure at 35° C. A sample of the residue was chromatographed on silica gel (200 g) with an ethyl acetate-:hexane (2:3) solvent. p-Hydroxymethyl-benzyl chloride was obtained in 75% yield (11.64 g). The product had a melting point of 58°–60° C. NMR spectral data were as follows: $^1$H NMR (CDCl$_3$, 300 MHz): δ7.3 (m, 4H), 4.70 (s, 2H), 4.59 (s, 2H), 1.67 (s, 1H); $^{13}$C NMR (CDCl$_3$, 75 MHz, ppm) 141.372, 135.995, 128.876, 127.366, 64.927, 46.121.

EXAMPLE 2 m-Hydroxymethylbenzyl chloride 1,3-benzenedimethanol (27.772 g, 0.201 mole) was charged to a 500 mL round-bottom flask equipped with a septum inlet and a nitrogen adapter connected to a gas scrubber. The mixture was placed in an ice bath and cooled to 0° C. Thionyl chloride (14.66 mL, 0.201 mole), dissolved in chloroform (200 mL) was added slowly via syringe and the mixture stirred at 0° C. for 15 minutes followed by continued stirring at room temperature for 18 hours. TLC analysis of a sample removed after one hour of stirring at room temperature showed little reaction product formed. After 18 hours, TLC analysis indicated that the product was present. The mixture was concentrated as in Example 1 and the residue purified on a silica gel column (700 g) using 1:3 ethyl acetate:hexane followed by 1:2 ethyl acetate:hexane. The title compound, m-hydroxymethylbenzyl chloride, was obtained as a colorless oil (19.39 g) in 61.6% yield.

The results of Examples 1 and 2 demonstrate that greater than 50% yields of hydroxy halides were obtained by the method of the invention.

EXAMPLE 3

3-(trimethylsilylethoxymethoxymethyl)benzyl chloride m-Hydroxymethylbenzyl chloride (19.29 g, 123.2 mmole) and N,N-diisopropylethylamine (43 mL, 246 mmole) in dichloromethane (150 mL) were placed in a 500 mL round bottom flask fitted with a reflux condenser and a dropping funnel. 2-(Trimethylsilyl)ethoxymethyl chloride (32.7 mL, 185 mmol) in dichloromethane (50 mL) was added slowly via the dropping funnel. After the addition was complete, the contents were heated at 55° C. for 18 hours, after which TLC using 1:5 ethyl acetate:hexane indicated completion of the reaction. The dichloromethane solution was cooled to room temperature, washed with water (100 mL) and then dried over anhydrous magnesium sulfate. After filtration and concentration, the residue was chromatographed on silica gel to provide 32.57 g (92% yield) of the desired product. $^1$H NMR spectral data were as follows: (CDCl$_3$, 300 MHz): δ7.3 (m, 4H), 4.8 (s, 2H), 4.65 (s, 2H), 4.6 (s, 2H), 3.65 (m, 2H), 1.0 (m, 2H), 0.00 (s, 9H).

EXAMPLE 4

4-(t-Butoxymethyl)benzyl chloride

A 5-gallon stirred pressure reactor was charged with p-hydroxymethylbenzyl chloride (600 g, 3.83 moles) in dichloromethane (6 liters). Concentrated sulfuric acid (60 mL) was charged to the reactor. Isobutylene gas was charged to the stirred solution for 2 hours at 10 psi. The temperature of the reaction was maintained at 20°–25° C. At the end of 24 hours the reaction was about 85% complete. The reaction mixture was diluted with water and the mixture adjusted to pH 7 by addition of 25% aqueous sodium hydroxide. The dichloromethane extract was dried over anhydrous sodium sulfate, filtered and concentrated under vacuum. The residue was fractionally distilled on a 24 cm Vigreux column to provide 312 g (45% yield) of the desired product. The boiling point of the product was 115°–125° C. (2–3 mm Hg). $^1$H NMR spectral data were as follows: (CDCl$_3$, 300 MHz): δ7.4 (s, 4H), 4.58 (s, 2H), 4.45 (s, 2H), 1.3 (s, 9H).

EXAMPLE 5

4-(Tetrahydropyranyloxymethyl)benzyl chloride p-Hydroxymethylbenzyl chloride (1.33 kg, 1 mole) in dichloromethane (6 liters) was charged to a 10 liter Morton flask. Addition of 3,4-dihydro-2H-pyran (925 g, 1.1 moles) to the flask was followed by cooling to 5° C. Pyridinium p-toluenesulfonate (1.25 g, 5 mmoles) was added as a catalyst. The contents were allowed to warm up to 20°–25° C. and stirred for 24 hours. The contents were washed with water followed by a sodium bicarbonate solution and then dried over anhydrous magnesium sulfate. The residue, after removal of solvent, was kept under high vacuum (1–2 mm Hg) for 24 hours and provided 2.28 kg (95% yield) of the desired product. $^1$H NMR spectral data were as follows: (CDCl$_3$, 300 MHz): δ7.4 (s, 4H), 4.75 (t, 1H), 4.65 (AB quartet, 2H, J=13 Hz), 4.6 (s, 2H), 3.85 (m, 1H), 3.55 (m, 1H), 1.5–1.95 (m, 6H).

EXAMPLE 6

4-(Methoxyethoxymethoxymethyl)benzyl chloride

A 5 liter round bottom flask, fitted with a reflux condensor, dropping funnel and mechanical stirrer, was charged with p-hydroxymethylbenzyl chloride (255 g, 1.91 moles) in dichloromethane (2 liters). The flask was charged with 2-methoxyethoxymethyl chloride (300 g, 2.41 moles) and stirred at 20°–25° C. while N,N-diisopropylethylamine (500 mL, 2.86 moles) was slowly added. The reaction became exothermic and caused the dichloromethane solvent to reflux vigorously for 20 minutes. The contents were then stirred for 24 hours at room temperature. The dichloromethane extract was washed with water and brine. The remaining organics were dried over anhydrous magnesium sulfate. After removal of the solvent by rotary evaporation, the residue was passed through a plug of silica gel to provide 310 g (67% yield) of the desired product. $^1$H NMR spectral data were as follows: (CDCl$_3$, 300 MHz): δ7.35 (m, 4H), 4.80 (s, 2H), 4.62 (s, 2H), 4.58 (s, 2H), 3.72 (m, 2H), 3.58 (m, 2H), 3.4 (s, 3H).

EXAMPLE 7

4-(Triphenylmethoxymethyl)benzyl chloride

A 100 mL round bottom flask was charged with triphenylmethyl methyl ether (2.74 g, 10 mmol), trityl chloride (2.79 g, 10 mmol), p-hydroxymethylbenzyl chloride (3.13 g, 20 mmol), toluene (12 mL), heptane (12 mL) and 32% HCl (2 drops). The solution was heated to reflux and 12 mL solvent was distilled over 2 hours. The solution was cooled to room temperature and the resulting slurry diluted with 12 mL heptane. After cooling in an ice bath, the product was isolated by vacuum filtration and dried in vacuo at 40° C. to give 6.27 g (79% yield) of crude product. Recrystallization from 20 mL acetonitrile gave 5.46 g (88% recovery) of the desired product. The product had a melting point of 126°–128° C. $^1$H NMR spectral data were as follows: (CDCl$_3$, 300 MHz): δ7.6–7.2 (complex, 19H), 4.6 (s, 2H), 4.2 (s, 2H).

The results of Examples 3–7 demonstrate that high yields of organooxy halides can be obtained by the method of the invention. Product yields in Examples 5, 6 and 7 were 95%, 67% and 70%, respectively.

EXAMPLE 7A

This relates to Examples 1 and 7, except the chlorination was run in methylene chloride, the intermediate p-hydroxymethylbenzyl alcohol was not isolated and triphenylmethyl alcohol was used as the source of the triphenylmethyl protecting group. 1,4-benzenedimethanol (69 g, 0.50 mole) was slurried in methylene chloride (550 mL) under nitrogen at 6°–8° C. Thionyl chloride (59.5 g, 500 mmol) was added over 2 hours, keeping the temperature below 10° C. The mixture was then allowed to warm to room temperature and stir 4 hours. Approximately half of the methylene chloride (250 mL) was then removed by atmospheric distillation. To the reaction vessel was added cyclohexane (250 mL) followed by triphenylmethyl alcohol (100.3 g, 385 mmol). Another 250 mL solvent was distilled followed by the addition of 250 mL fresh cyclohexane. This distillation procedure was repeated four times. The final pot temperature was 74° C. Cyclohexane (350 mL) was added and the mixture cooled to 15°–18° C. and held for 3 hr. The product was isolated by vacuum filtration, washed once with cold cyclohexane (50 mL) and dried in vacuo at 50° C. to give 130 g (65% yield) of crude product. A 100 g portion of this material was recrystallized from 200 mL acetonitrile to give 85 g (85% recovery) of the desired product. The product had a melting point of 125.5°–127° C.

EXAMPLE 8

Alkylation of cyclic urea nitrogens

A three-neck 3 liter Morton flask equipped with an addition funnel, a mechanical stirrer and a nitrogen inlet was charged with a compound of formula (IV) (250 g, 0.4 mole), where $R^4$ and $R^7$ are benzyl and $R^5$ and $R^6$ are 2-methoxyethoxymethyl, and q is 1, in 1 liter of 1,3-dimethyl-3,4,5,6-tetrahydro-2(1H)-pyrimidinone (DMPU) and cooled to 0° C. Sodium hydride (48 g, 1.2 moles of a 60% dispersion in mineral oil) was added in small batches to the cooled mixture with stirring. Hydrogen gas was evolved. The mixture was stirred at room temperature for 30 minutes and then cooled to 0° C. An alkylating agent of the formula (I) (240 g, 1 mole), where Q is 1,4-disubstituted phenyl, Y and Z are hydrogen, m and n are 1 and $R^3$ is tetrahydropyranyl, in 250 mL DMPU was added to the stirred mixture and stirring was continued for 18 hours at room temperature. The mixture was then cooled to 0° C. and quenched with saturated ammonium chloride. Hydrogen gas was evolved. The quenched mixture was diluted with water and extracted with two 750 mL volumes of ethyl acetate. The organic extracts were combined, washed with water and dried over anhydrous magnesium sulfate. The solvent was removed by rotary evaporation.

To acid-deprotect the compound, the residue was resuspended in 200 mL anhydrous methanol and added with stirring to a 2 liter round bottom flask containing 1 liter of a 2M solution of anhydrous hydrogen chloride in anhydrous methanol. The mixture was stirred at room temperature for 18 hours and then quenched and neutralized with a solution of sodium bicarbonate. The quenched mixture was extracted with ethyl acetate and dried over anhydrous magnesium sulfate. The solvent was removed to yield 250 g of crude deprotected product. The product was triturated in 250 mL ethyl acetate, allowed to stand for 2 hours and filtered to provide 130 g of the desired product, namely, a compound of formula (V) where $R^3$ is hydroxy, $R^4$ and $R^7$ are benzyl, $R^5$ and $R^6$ are hydroxy, Y and Z are hydrogen and m, n and q are 1. The mother liquor was purified by column chromatography to provide an additional 70 g of product. The solids were combined and crystallized from hot acetonitrile to provide 160 g of the product. The melting point of the product was 195°–197° C. High resolution mass spectroscopy (chemical ionization) indicated $M+H^+$ of 567.2869.

EXAMPLE 9

Alkylation of cyclic urea nitrogens

A 30 liter glass reactor was charged with a compound of formula (IV) (975 g, 2.66 moles), where $R^4$ and $R^7$ are benzyl and $R^5$ and $R^6$ are the cyclic acetonide, 4-(triphenylmethoxy)benzyl chloride (2.28 kg, 5.72 moles) and tetrahydrofuran (2.83 liters). A solution of 1.6N potassium t-butoxide in tetrahydrofuran (3960 mL, 6.3 moles) was added over 2 hours while maintaining the temperature at 20°14 35° C. The resulting solution was stirred at room temperature overnight. Water (527 mL) was added over 5 minutes followed by Celite® 545 (135 g) 15 minutes later. The slurry was stirred 15 minutes then clarified by vacuum filtration. The filtrate was stirred vigorously and diluted with methanol (6.83 L). The solution was seeded and the product allowed to crystallize at room temperature. Additional methanol (3.41 L) was added and the slurry was cooled to 6° C. over six hours and filtered. The product was washed with a mixture of methanol and THF, then twice with methanol and dried to give 2.66 kg (91% Yield) of the triphenylmethyl/acetonide protected product. The melting point of the product was 204.2°–206.6° C. $^1$H NMR (CDCl$_3$) $\delta$1.33 (s, 6H), 2.95 (d, 4H, J=7 Hz), 3.07 (d, 2H, J=14 Hz), 3.82 (mult, 4H), 4.15 (s, 4H), 4.96 (d, 2H, J=14 Hz), 7.1–7.5 (complex, 48 H).

To acid deprotect the compound, 2.20 kg of the material was stirred for three hours in a 30 liter reactor with toluene (4.40 L), methanol (11.0 L) and 32% hydrochloric acid (181 mL). To the stirred solution was added heptanes (4.4 L), 30% sodium hydroxide (190 mL), and water (4.4 L). The phases were allowed to separate and the lower aqueous phase was reextracted with a mixture of heptanes and toluene, then finally with heptanes. The aqueous phase was stirred vigorously and 60 mL 32% hydrochloric acid followed by water (1,10 liter) was added. After solids began to crystallize, 4.71 L additional water was added and the slurry was stirred at room temperature overnight, then cooled to 7° C. and filtered. The product was washed with water and dried to give 1.12 kg (100% yield) of crude product. Recrystallization from methanol/toluene then ethanol/water gave 1.03 kg (92% yield) of the pure product. The melting point of the product was 205°–206° C. $^1$H NMR spectral data were as follows: (CD$_3$OD, 300 MHz): $\delta$7.2–7.0 (complex, 16H), 4.88 (s, 4H), 4.75 (d, 2H, J=11 Hz), 4.55 (s, 4H), 3.57 (brd, 2H), 3.52 (brs, 2H), 3.30 (brs, 2H), 3.1–2.85 (complex, 6H).

As demonstrated in Examples 8 and 9, the method of the invention is effective for alkylating cyclic urea compounds.

The present invention may be embodied in other specific forms without departing from the spirit or essential attributes thereof.

What is claimed is:

1. A process for preparing a hydroxy halide alkylating agent or an organooxy halide alkylating agent of formula (I):

 (I)

wherein:
Q is selected from the following:
$C_1$-$C_8$ alkyl substituted with 0–3 $R^{31}$;
$C_2$-$C_8$ alkenyl substituted with 0–3 $R^{31}$;
$C_2$-$C_8$ alkynyl substituted with 0–3 $R^{31}$;
a $C_3$-$C_{14}$ carbocyclic ring system substituted with 0–5 $R^{31}$ or 0–5 $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

$R^{31}$ is selected independently from:
cyano, —CH$_2$NR$^{13}$R$^{14}$, —NR$^{13}$R$^{14}$, —OR$^{13}$, $C_2$-$C_6$ alkoxyalkyl, —S(O)$_m$R$^{13}$, —C(=O)NR$^{13}$R$^{14}$, —NR$^{14}$C(=O) R$^{13}$, —NR$^{14}$C(=O)OR$^{14}$, —OC(=O)NR$^{13}$R$^{14}$, —NR$^{13}$C(=O)NR$^{13}$R$^{14}$, —NR$^{13}$C(=S)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, $C_1$-$C_4$ alkyl, $C_2$-$C_4$ alkenyl, $C_3$-$C_{10}$ cycloalkyl, $C_3$-$C_6$ cycloalkylmethyl, benzyl, phenethyl, phenoxy, benzyloxy, nitro, $C_7$-$C_{10}$ arylalkyl, formyl, $C_3$-$C_6$ cycloalkoxy, $C_1$-$C_4$ alkyl substituted with —NR$^{13}$R$^{14}$, $C_1$-$C_4$ alkoxycarbonyl, $C_1$-$C_4$ alkylcarbonyloxy, $C_1$-$C_4$ alkylcarbonyl, —OCH$_2$CO$_2$R$^{13}$, 2-(1-morpholino)ethoxy, azido, —C(R$^{14}$)=N(OR$^{14}$); or
1–3 amino acids, linked together via amide bonds, said amino acid being linked via the amine or carboxylate terminus;
a $C_5$-$C_{14}$ carbocyclic residue substituted with 0–5 $R^{32}$; or
a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$-$C_{10}$ cycloalkyl, $C_3$-$C_6$ cycloalkylmethyl, $C_7$-$C_{10}$ arylalkyl, benzyl protected oxime, $C_2$-$C_6$ alkoxyalkyl, methylenedioxy, ethylenedioxy, $C_1$-$C_4$ alkylcarbonyloxy, —NHSO$_2$R$^{14}$, benzyloxy, 2-(1-morpholino)ethoxy, —CONR$^{13}$NR$^{13}$R$^{14}$, cyano, sulfonamide, $C_3$-$C_6$ cycloalkoxy, —NR$^{13}$R$^{14}$, —C(R$^{14}$)=N(OR$^{14}$), —NO$_2$, —OR$^{13}$, —NR$^{40}$R$^{41}$, —SR$^{13}$, —SOR$^{13}$, —SO$_2$R$^{13}$, —SNR$^{13}$R$^{14}$, —SONR$^{13}$R$^{14}$, —SO$_2$NR$^{13}$R$^{14}$, —C(=O)NR$^{13}$R$^{14}$, —OC(=O)NR$^{13}$R$^{14}$, —C(=O)R$^{11}$, phenyl, —C(=O)NR$^{13}$-(C$_1$-C$_4$ alkyl)-NR$^{13}$R$^{14}$, —C(=O)NR$^{40}$R$^{41}$, —C(=O)NR$^{13}$C(R$^{11}$)$_2$NR$^{13}$R$^{14}$; —C(=O)NR$^{13}$C(R$^{11}$)$_2$NR$^{13}$CO$_2$R$^{13}$; —C(=O)NR$^{13}$-(C$_1$-C$_4$ alkyl)-NR$^{13}$CO$_2$R$^{13}$; —C(=O)N(R$^{13}$)-(C$_1$-C$_4$ alkyl)-R$^{11}$; or —C(=O)C(R$^{11}$)$_2$NR$^{13}$R$^{14}$; —C(=O)C(R$^{11}$)$_2$NR$^{13}$CO$_2$R$^{13}$; —C(=O)-(C$_1$-C$_4$ alkyl)-NR$^{13}$R$^{14}$; —C(=O)-(C$_1$-C$_4$ alkyl)-NR$^{13}$CO$_2$R$^{13}$; or
$C_1$-$C_4$ alkoxy substituted with 0–4 groups selected from: R$^{11}$, $C_3$-$C_6$ cycloalkyl, —CO$_2$R$^{13}$, —C(=O)NR$^{13}$R$^{14}$, —NR$^{13}$R$^{14}$ or OH;

$C_1$–$C_4$ alkyl substituted with 0–4 groups selected from: $R^{11}$, $=NR^{14}$, $=NNR^{13}C(=O)NR^{13}R^{14}$, $=NNR^{13}C(=O)OR^{13}$, or $-NR^{13}R^{14}$;

$C_2$–$C_4$ alkenyl substituted with 0–4 $R^{11}$;

$C_2$–$C_4$ alkynyl substituted with 0–4 $R^{11}$;

a 5- or 6-membered heterocyclic ring containing from 1 to 4 heteroatoms independently selected from oxygen, nitrogen or sulfur, substituted with 0–2 $R^{12}$;

or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, benzyloxy, or $-NR^{13}R^{14}$; or, when $R^{32}$ is attached to a saturated carbon atom, it may be $=O$, $=S$, $=N$O-benzyl; or when $R^{32}$ attached to sulfur it may be $=O$;

$R^{32}$ when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, $-CH_2NR^{13}R^{14}$, $-NR^{13}R^{14}$, $C_2$–$C_6$ alkoxyalkyl, $C_1$–$C_4$ alkylcarbonyl, $-C(R^{14})=N(OR^{14})$;

$R^{40}$ is selected from: H, $C_1$–$C_3$ alkyl;

$R^{41}$ is selected from:
$-C(=O)NR^{13}R^{14}$;
$-C(=O)NR^{13}NR^{13}R^{14}$;
$-C(=O)C(R^{11})_2NR^{13}R^{14}$;
$-C(=O)C(R^{11})_2NR^{13}NR^{13}R^{14}$;
$-C(=O)C(R^{11})_2NR^{13}CO_2R^{13}$;
$-C(=O)H$;
$-C(=O)R^{11}$;
$-C(=O)-(C_1-C_4$ alkyl)$-NR^{13}R^{14}$; $-C(=O)-(C_1-C_4$ alkyl)$-NR^{13}CO_2R^{13}$;
1–3 amino acids linked together via amide bonds, and linked to the N atom via the carboxylate terminus;

$R^{11}$ is selected from one or more of the following:
H, keto, cyano, $-CH_2NR^{13}R^{14}$, $-NR^{13}R^{14}$, $-OR^{13}$, $-S(O)_m R^{13}$, $-NR^{14}C(=O)R^{13}$, $=NOR^{14}$, $-NR^{14}C(=O)OR^{14}$, $-OC(=O)NR^{13}R^{14}$, $-NR^{13}C(=O)NR^{13}R^{14}$, $-NR^{14}SO_2NR^{13}R^{14}$, $-NR^{14}SO_2R^{13}$, $-SO_2NR^{13}R^{14}$, $-OP(O)(OR^{13})_2$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, formyl, $C_3$–$C_6$ cycloalkoxy, $C_1$–$C_4$ alkyl substituted with $-NR^{13}R^{14}$, $C_1$–$C_4$ benzyloxyalkyl, methylenedioxy, ethylenedioxy, $C_1$–$C_4$ alkylcarbonyl, $C_1$–$C_4$ alkylcarbonylamino, 2-(1-morpholino)ethoxy, azido, or $-C(R^{14})=N(OR^{14})$;

1–3 amino acids linked together via amide bonds, said amino acid being linked via the amine or carboxylate terminus;

$C_3$–$C_{10}$ cycloalkyl substituted with 0–2 $R^{12}$;

$C_1$–$C_4$ alkyl substitued with 0–2 $R^{12}$ aryl($C_1$–$C_3$ alkyl)-, substituted with 0–2 $R^{12}$;

$C_2$–$C_6$ alkoxyalkyl-, substituted with 0–2 $R^{12}$;

$C_1$–$C_4$ alkylcarbonyloxy substituted with 0–2 $R^{12}$, $C_6$–$C_{10}$ arylcarbonyloxy substituted with 0–2 $R^{12}$, a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{114}$ is selected from one or more of the following:
H, keto, cyano, $-CH_2N(R^{134})R^{(144)}$, $-N(R^{134})R^{(144)}$, $-CO_2H$, $-OC(=O)(C_1-C_3$ alkyl), $-O$benzyl, $C_2$–$C_6$ alkoxyalkyl, $-C(=O)NH_2$, $-OC(=O)NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system substituted with 0–3 $R^{124}$;

$R^{12}$, when a substituent on carbon, is selected from one or more of the following:

phenyl, benzyl, phenethyl, phenoxy, benzyloxy, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, $-OR^{13}$, $C_1$–$C_4$ alkyl substituted with $-NR^{13}R^{14}$, $-NR^{13}R^{14}$, $C_2$–$C_6$ alkoxyalkylene optionally substituted with $-Si(CH_3)_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, $-SR^{13}$, $-SOR^{13}$, $-SO_2R^{13}$, $-SO_2NR^{13}R^{14}$, $-NHSO_2R^{14}$, $-OCH_2CO_2R^{13}$, 2-(1-morpholino)ethoxy, $-C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, hydroxy, or $-NR^{13}R^{14}$; or, when $R^{12}$ is attached to a saturated carbon atom, it may be $=O$ or $=S$; or when $R^{12}$ is attached to sulfur it may be $=O$;

$R^{12}$, when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, $-CH_2NR^{13}R^{14}$, $-NR^{13}R^{14}$, $C_2$–$C_6$ alkoxyalkyl, $C_1$–$C_4$ alkylcarbonyl, $-C(R^{14})=N(OR^{14})$;

$R^{124}$, when a substituent on carbon, is selected from one or more of the following:

phenyl, benzyl, phenethyl, phenoxy, benzyloxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, formyl, $C_3$–$C_6$ cycloalkoxy, $-OR^{13}$, $C_2$–$C_6$ alkoxyalkyl optionally substituted with $-Si(CH_3)_3$, $C_1$–$C_4$ benzyloxyalkyl, methylenedioxy, ethylenedioxy, $C_1$–$C_4$ alkylcarbonyl, $C_1$–$C_4$ alkylcarbonylamino, $-SMe$, $-S(=O)$ Me, $-SO_2Me$, $-OCH_2CO_2R^{13}$, 2-(1-morpholino)ethoxy; or a 5- or 6-membered heterocyclic ring containing from 1 to 4 heteroatoms independently selected from oxygen, nitrogen or sulfur;

or $R^{124}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, benzyloxy; or, when $R^{12A}$ is attached to a saturated carbon atom, it may be =O or =S; or when $R^{12}$ is attached to sulfur it may be =O;

$R^{12A}$, when a substituent on nitrogen, is selected from one or more of the following:

phenyl, benzyl, phenethyl, benzyloxy, $C_1$-$C_4$ benzyloxyalkyl, $C_1$-$C_4$ alkoxy, $C_1$-$C_4$ alkyl, $C_3$-$C_6$ cycloalkyl, $C_3$-$C_6$ cycloalkylmethyl, $C_2$-$C_6$ alkoxyalkyl, $C_1$-$C_4$ alkylcarbonyl;

$R^{13}$ is selected from:
phenyl substituted with 0–3 $R^{11A}$;
benzyl substituted with 0–3 $R^{11A}$;
$C_1$-$C_6$ alkyl substituted with 0–3 $R^{11A}$;
$C_2$-$C_4$ alkenyl substituted with 0–3 $R^{11A}$;
$C_1$-$C_6$ alkylcarbonyl substituted with 0–3 $R^{11A}$;
$C_1$-$C_6$ alkoxycarbonyl substituted with 0–3 $R^{11A}$;
$C_1$-$C_6$ alkylaminocarbonyl substituted with 0–3 $R^{11A}$;
$C_3$-$C_6$ alkoxyalkyl substituted with 0–3 $R^{11A}$;
an amine protecting group when $R^{13}$ is bonded to N;
a hydroxy protecting group when $R^{13}$ is bonded to O;

$R^{14}$ is benzyloxy, $C_1$-$C_6$ alkyl substituted with 0–3 groups selected from —Obenzyl, $C_1$-$C_4$ alkoxy, $C_1$-$C_6$ alkoxy, $C_2$-$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{13A}$ and $R^{14A}$ are independently selected from: H, $C_1$-$C_6$ alkyl;

$R^{13A}$ and $R^{14A}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{15}$ is H or CH$_3$;
X is chloro, bromo or iodo;
$R^3$ is a hydroxy protecting group; and
m and n are independently 1, 2 or 3;
said process comprising the steps of:
(1) reacting an organodiol of formula (II):

wherein Q, m and n are as defined above for formula (I), with a halogenating reagent in a chlorinated organic solvent, with the proviso that the halogenating reagent is not a hydrogen halide, to form a compound of formula (IA):

wherein Q, X, m, and n are as defined above for formula (I); and (2) reacting compound (IA) with a reagent suitable for the protection of hydroxy groups to form the compound of formula (I) wherein $R^3$ is a hydroxy protecting group.

2. A process of claim 1 for preparing an alkylating agent compound of formula (I) wherein:

Q is selected from:
$C_1$-$C_8$ alkyl substituted with 0–3 $R^{31}$;
$C_2$-$C_8$ alkenyl substituted with 0–3 $R^{31}$;
$C_2$-$C_8$ alkynyl substituted with 0–3 $R^{31}$;
a $C_3$-$C_{14}$ carbocyclic ring system substituted with 0–5 $R^{31}$ or 0–5 $R^{32}$;

$R^{31}$ is selected from one or more of the following:
cyano, —CH$_2$NR$^{13}$R$^{14}$, —NR$^{13}$R$^{14}$, —OR$^{13}$, $C_2$-$C_6$ alkoxyalkyl, —SR$^{13}$, —SOR$^{13}$, —SO$_2$R$^{13}$, $C_1$-$C_4$ alkyl, $C_2$-$C_4$ alkenyl, $C_3$-$C_{10}$ cycloalkyl, $C_3$-$C_6$ cycloalkylmethyl, benzyl, phenethyl, phenoxy, benzyloxy, nitro, $C_7$-$C_{10}$ arylalkyl, formyl, $C_3$-$C_6$ cycloalkoxy, $C_1$-$C_4$ alkyl substituted with —NR$^{13}$R$^{14}$, $C_1$-$C_4$ alkoxycarbonyl, $C_1$-$C_4$ alkylcarbonyloxy, $C_1$-$C_4$ alkylcarbonyl, —OCH$_2$CO$_2$R$^{13}$, 2-(1-morpholino)ethoxy, azido, —C(R$^{14}$)=N(OR$^{14}$); or a $C_5$-$C_{14}$ carbocyclic residue substituted with 0–5 $R^{32}$; or aryl substituted with 0–3 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$-$C_{10}$ cycloalkyl, $C_3$-$C_6$ cycloalkylmethyl, $C_7$-$C_{10}$ arylalkyl, benzyl protected oxime, $C_2$-$C_6$ alkoxyalkyl, methylenedioxy, ethylenedioxy, $C_1$-$C_4$ alkylcarbonyloxy, —NHSO$_2$R$^{14}$, benzyloxy, 2-(1-morpholino)ethoxy, cyano, sulfonamide, $C_3$-$C_6$ cycloalkoxy, —NR$^{13}$R$^{14}$, —C(R$^{14}$)=N(OR$^{14}$), —NO$_2$, —OR$^{13}$, —NR$^{40}$R$^{41}$, —SO$_p$R$^{13}$, —SNR$^{13}$R$^{14}$, —SONR$^{13}$R$^{14}$, —SO$_2$NR$^{13}$R$^{14}$, —C(=O)NR$^{13}$R$^{14}$, —OC(=O)NR$^{13}$R$^{14}$, —C(=O)R$^{11}$, phenyl, —C(=O)NR$^{13}$-(C$_1$-$C_4$ alkyl)-NR$^{13}$R$^{14}$, —C(=O)NR$^{40}$R$^{41}$;
—C(=O)NR$^{13}$C(R$^{11}$)$_2$NR$^{13}$R$^{14}$;
—C(=O)NR$^{13}$C(R$^{11}$)$_2$NR$^{13}$CO$_2$R$^{13}$;
—C(=O)NR$^{13}$-(C$_1$-$C_4$ alkyl)-NR$^{13}$CO$_2$R$^{13}$;
—C(=O)N(R$^{13}$)-(C$_1$-$C_4$ alkyl)-R$^{11}$; or
—C(=O)C(R$^{11}$)$_2$NR$^{13}$R$^{14}$;
—C(=O)C(R$^{11}$)$_2$NR$^{13}$CO$_2$R$^{13}$; —C(=O)—(C$_1$-$C_4$ alkyl)-NR$^{13}$R$^{14}$; —C(=O)-(C$_1$-$C_4$ alkyl)-NR$^{13}$CO$_2$R$^{13}$; or $C_1$-$C_4$ alkoxy substituted with 0–4 groups selected from: $R^{11}$, $C_3$-$C_6$ cycloalkyl, —CO$_2$R$^{13}$, —C(=O)NR$^{13}$R$^{14}$, —NR$^{13}$R$^{14}$ or benzyloxy;

$C_1$-$C_4$ alkyl substituted with 0–4 groups selected from: $R^{11}$, =NR$^{14}$, =NNR$^{13}$C(=O)NR$^{13}$R$^{14}$, or —NR$^{13}$R$^{14}$;

$C_2$-$C_4$ alkenyl substituted with 0–4 $R^{11}$;
$C_2$-$C_4$ alkynyl substituted with 0–4 $R^{11}$;

a 5- or 6-membered heterocyclic ring containing from 1 to 4 heteroatoms independently selected from oxygen, nitrogen or sulfur, substituted with 0–2 $R^{12}$;

or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1$-$C_4$ alkyl, $C_1$-$C_4$ alkoxy, benzyloxy, or —NR$^{13}$R$^{14}$; or, when $R^{32}$ is attached to a saturated carbon atom, it may be =O, =S, =NO-benzyl; or when $R^{32}$ attached to sulfur it may be =O;

$R^{32}$, when a substituent on nitrogen, is selected from one or more of the following:
phenyl, benzyl, phenethyl, benzyloxy, $C_1$-$C_4$ benzyloxyalkyl, $C_1$-$C_4$ alkoxy, $C_1$-$C_4$ alkyl, $C_3$-$C_6$ cycloalkyl, $C_3$-$C_6$ cycloalkylmethyl, —CH$_2$NR$^{13}$R$^{14}$, —NR$^{13}$R$^{14}$, $C_2$-$C_6$ alkoxyalkyl, $C_1$-$C_4$ alkylcarbonyl, —C(R$^{14}$)=N(OR$^{14}$);

$R^{40}$ is selected from: H, $C_1$-$C_3$ alkyl;
$R^{41}$ is selected from:

—C(=O)NR$^{13}$R$^{14}$;
—C(=O)NR$^{13}$NR$^{13}$R$^{14}$;
—C(=O)C(R$^{11}$)$_2$NR$^{13}$R$^{14}$;
—C(=O)C(R$^{11}$)$_2$NR$^{13}$NR$^{13}$R$^{14}$;
—C(=O)C(R$^{11}$)$_2$NR$^{13}$CO$_2$R$^{13}$;
—C(=O)H;
—C(=O)R$^{11}$;
—C(=O)—(C$_1$-C$_4$ alkyl)-NR$^{13}$R$^{14}$;
—C(=O)—(C$_1$-C$_4$ alkyl)-NR$^{13}$CO$_2$R$^{13}$;

1-3 amino acids linked together via amide bonds, and linked to the N atom via the carboxylate terminus;

R$^{11}$ is selected from one or more of the following:
H, keto, cyano, —CH$_2$NR$^{13}$R$^{14}$, —NR$^{13}$R$^{14}$, —OR$^{13}$, —SR$^{13}$, —SOR$^{13}$, —SO$_2$R$^{13}$, C$_1$-C$_4$ alkyl, C$_2$-C$_4$ alkenyl, C$_3$-C$_{10}$ cycloalkyl substituted with 0–2 R$^{12}$ a C$_5$-C$_{14}$ carbocyclic residue substituted with 0–3 R$^{12}$, aryl(C$_1$-C$_3$ alkyl)-, substituted with 0–2 R$^{12}$, aryl substituted with 0–3 R$^{12}$; or a 5- to 10-membered heterocyclic ring system containing 1 to 4 heteroatoms independently selected from oxygen, nitrogen or sulfur, said heterocyclic ring system being substituted with 0–3 R$^{12}$;

R$^{12}$, when a substituent on carbon, is selected from one or more of the following:
phenyl, benzyl, phenethyl, phenoxy, benzyloxy, hydroxy, nitro, cyano, C$_1$-C$_4$ alkyl, C$_3$-C$_6$ cycloalkyl, C$_3$-C$_6$ cycloalkylmethyl, C$_7$-C$_{10}$ arylalkyl, C$_1$-C$_4$ alkoxy, sulfonamide, formyl, C$_3$-C$_6$ cycloalkoxy, —OR$^{13}$, C$_1$-C$_4$ alkyl substituted with —NR$^{13}$R$^{14}$, —NR$^{13}$R$^{14}$, C$_2$-C$_6$ alkoxyalkyl optionally substituted with —Si(CH$_3$)$_3$, C$_1$-C$_4$ benzyloxyalkyl, methylenedioxy, ethylenedioxy, C$_1$-C$_4$ alkoxycarbonyl, C$_1$-C$_4$ alkylcarbonyloxy, C$_1$-C$_4$ alkylcarbonyl, C$_1$-C$_4$ alkylcarbonylamino, —SR$^{13}$, —SOR$^{13}$, —SO$_2$R$^{13}$, —SO$_2$NR$^{13}$R$^{14}$, —NHSO$_2$R$^{14}$, 2-(1-morpholino)ethoxy, —C(R$^{14}$)=N(OR$^{14}$); or a 5- or 6-membered heterocyclic ring containing from 1 to 4 heteroatoms independently selected from oxygen, nitrogen or sulfur;

or R$^{12}$ may be a 3- or 4- carbon chain attached to adjacent carbons on the ring to form a fused 5- or 6-membered ring, said 5- or 6- membered ring being optionally substituted on the aliphatic carbons with C$_1$-C$_4$ alkyl, C$_1$-C$_4$ alkoxy, hydroxy, or —NR$^{13}$R$^{14}$; or, when R$^{12}$ is attached to a saturated carbon atom, it may be =O or =S; or when R$^{12}$ is attached to sulfur it may be =O;

R$^{12}$, when a substituent on nitrogen, is selected from one or more of the following:
phenyl, benzyl, phenethyl, benzyloxy, C$_1$-C$_4$ benzyloxyalkyl, C$_1$-C$_4$ alkoxy, C$_1$-C$_4$ alkyl, C$_3$-C$_6$ cycloalkyl, C$_3$-C$_6$ cycloalkylmethyl, —CH$_2$NR$^{13}$R$^{14}$, —NR$^{13}$R$^{14}$, C$_2$-C$_6$ alkoxyalkyl, C$_1$-C$_4$ alkylcarbonyl, —C(R$^{14}$)=N(OR$^{14}$);

R$^{13}$ is C$_1$-C$_6$ alkyl; C$_3$-C$_6$ alkoxyalkyl; C$_2$-C$_4$ alkenyl; phenyl; or benzyl;

R$^{14}$ is benzyloxy, C$_1$-C$_6$ alkyl, C$_1$-C$_6$ alkoxy, C$_2$-C$_6$ alkenyl, phenyl, benzyl, an amine protecting group when R$^{14}$ is bonded to N, or a hydroxy protecting group when R$^{14}$ is bonded to O;

R$^{15}$ is H or CH$_3$;

X is chloro, bromo or iodo;

R$^3$ is a hydroxy protecting group;

m and n are independently 1, 2 or 3.

3. A process of claim 1 wherein:
Q is selected from: allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, phenyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorophenyl, quinolinylmethyl, carboxyphenyl, benzyloxyphenyl, phenylphenyl, adamantylethyl, cyclopropylmethoxyphenyl, methoxyphenyl, methylphenyl, ethoxyphenyl, benzyloxymethylphenyl, N-protected aminophenyl, formylphenyl, cyanophenyl, cinnamyl, allyloxyphenyl, fluorophenyl, difluorophenyl, fluoromethylphenyl, cyclobutylmethyl, cyclopentylmethyl, nitrophenyl, (H$_2$NC(=O))-phenyl, carbomethoxyphenyl, carboethoxyphenyl, tetrazolylphenyl, and dimethylallyl, N-protected aminomethylphenyl, (O-benzyl-formaldoxime)phenyl, (O-methyl-formaldoxime)phenyl, (CH$_3$O$_2$CO)-phenyl, (benzyl-OCH$_2$CH$_2$N=CH)-phenyl, N-benzylaminocarbonylphenyl, N-protected N-methylaminophenyl, N-protected N-ethylaminophenyl, N-protected N-ethylaminomethylphenyl, acetylphenyl, acetoxyphenyl, N-benzyloxylaminophenyl, N-benzyloxylaminomethylphenyl, (benzyloxyl)ethylphenyl, (CH$_3$C(=NO-benzyl))-phenyl, (H$_2$NNHC(=O))-phenyl, (H$_2$NC(=O)NHN=CH)-phenyl, (CH$_3$ONHC(=O))-phenyl, (HONHC(=O))-phenyl, (CH$_3$NHC(=O))-phenyl, N,N-dimethylaminocarbonylphenyl, (benzyl-OCH$_2$CH(OH)CH$_2$O)-phenyl, benzyloxyethoxyphenyl, (oxazolidinyl)-phenyl, (benzyloxyl)hexyl, hexenyl, (benzyloxy)octyl, (benzyloxyl)pentyl, (carboxy)pentyl, (carbomethoxy)pentyl, (methylthio)phenyl, (methylsulfonyl)phenyl, N,N-dimethylaminomethylphenyl, N-protected N-methylaminomethylphenyl, glycylaminophenyl, N,N-dimethylglycylaminophenyl, alanylaminophenyl, (N-phenylmethoxycarbonyl)alanylaminophenyl, phenylalanylaminophenyl, (N-phenylmethoxycarbonyl)phenylalanylaminophenyl, (CH$_3$CH$_2$NHC(=O))-phenyl, N,N-diethylaminocarbonylphenyl, N-ethylaminocarbonylphenyl, N-propylaminocarbonylphenyl, N,N-diisopropylaminocarbonylphenyl, N,N-di-n-propylaminocarbonylphenyl, (benzyloxypropynyl)phenyl, (imidazolyl-C(=O))-phenyl, (pyrazolyl-C(=O))-phenyl, (pyridylmethylaminocarbonyl)phenyl, (oxadiazolidinonyl)phenyl, trifluoroacetylphenyl, (pyrazolyl)phenyl, (H$_2$NSO$_2$)-phenyl, dibenzyloxyethylphenyl, (MeHNC(=O)NH)-phenyl, (H$_2$NC(=O)NH)-phenyl, (HC(=O)NH)-phenyl, methanesulfonylpentyl, methoxypentyl, N-formyl-N-methylaminophenyl, acetylaminophenyl, propionylphenyl, butyrylphenyl, (CH$_3$CH$_2$C(=NObenzyl))-phenyl, (trifluorohydroxyethyl)phenyl, (CF$_3$C(=NOH))-phenyl, (N-methylglycyl)aminophenyl, ((4-morpholino)ethyl)

aminocarbonylphenyl, (N,N-dimethylaminoethyl) aminocarbonylphenyl, (N,N-diethylaminoethyl) aminocarbonylphenyl, (4-methylpiperazin-1-ylethyl) aminocarbonylphenyl, (benzyl-NHC(=O)O)phenyl, (CH$_3$NHC(=O)O)phenyl, (NH$_2$C(=O)CH$_2$O)phenyl, (NH$_2$C(=NH))phenyl, ((N-phenylmethoxycarbonyl) glycylamino)phenyl, (imidazolylmethyl)phenyl, ((CH$_3$)$_3$C-C(=O))phenyl, (N-methyl-N-ethylaminoethyl)aminocarbonylphenyl, (pyrrolidinylethyl)aminocarbonylphenyl, (piperidinylethyl)aminocarbonylphenyl, (H$_2$NC(=NObenzyl))phenyl, (H$_2$NC(=NObenzyl)) fluorophenyl, benzimidazolylmethyl, benzotriazolylmethyl, indazolylmethyl, benzoxazolinylmethyl, benzisoxazolylmethyl, thienylmethyl, or furylmethyl;

m and n are independently 1, 2 or 3;

X is chloro, bromo or iodo;

R$^3$ is a hydroxy protecting group.

4. A process of claim 1 for preparing an alkylating agent compound of formula (I) wherein:

Q is selected from:
allyl, propyl, cyclopropylmethyl, n-hexyl, n-butyl, CH$_2$CH=C(CH$_3$)$_2$, methallyl, i-pentyl, phenyl, hexyl, isoprenyl, cinnamyl, fluorophenyl, (methylsulfonyl)phenyl, cyclopropylmethyl, naphthylmethyl, 4-pyridinylmethyl, 2-pyridinylmethyl, carboxypentyl, cyclopentylmethyl, cyanophenyl, quinolinylmethyl, vinylphenyl, methylphenyl, carbomethoxyphenyl, formylphenyl, (O-benzylformaldoxime)phenyl, cyclobutylmethyl, difluorophenyl, nitrophenyl, N-protected aminomethylphenyl, 3-(NHCHO) phenyl, benzyloxyphenyl, N-benzyloxyaminomethylphenyl, 3-(CH$_3$OC(=O) O-)phenyl, 3-(1-benzyloxyethyl)phenyl, 3-(HOCH$_2$CH$_2$N=CH)phenyl, 3-(2-oxazolidinyl) phenyl, 3-(C$_6$H$_5$CH$_2$NHC(=O)O)phenyl, 3-(CH$_3$NHC(=O)O)phenyl, acetylphenyl, (CH$_3$C(=NO-benzyl))-phenyl, 2-(hydroxymethyl)-cyclopropylmethyl, (H$_2$NNHC(=O))-phenyl, (H$_2$NC(=O)NHN=CH)-phenyl, 3-[(N-methoxy) aminocarbonyl]-phenyl, 4-[(N-methoxy) aminocarbonyl]-phenyl, benzyloxyethoxyphenyl, (benzyl-OCH$_2$CH(Obenzyl)CH$_2$O)-phenyl, (NH$_2$C(=NH))phenyl, (methylaminocarbonyl)phenyl, 3-formyl-phenyl, 3-(1-benzyloxyethyl)phenyl, (methylaminocarbonyl)phenyl, (H$_2$NC(=O) NH)-phenyl, N-protected N-methylaminophenyl, N-protected aminophenyl, N,N-dimethylaminophenyl, 3-propionylphenyl, (CH$_3$NHC(=O)NH)-phenyl, 3-(2-imidazolyl-C(=O))phenyl, 3-(CH$_3$CH$_2$C(=N—O-benzyl)) phenyl, N,N-dimethylglycylaminophenyl, 3-((N-phenylmethoxycarbonylaminoglycyl)amino)phenyl, 3-((N-phenylmethoxycarbonylamino-L-alanyl) amino)phenyl, 3-((N-phenylmethoxycarbonylamino-L-phenylalanyl) amino)phenyl, 3-(CF$_3$CH$_2$C(=N—Obenzyl)) phenyl, alanylaminophenyl, phenylalanylaminophenyl, (methylsulfonyl)pentyl, N-protected N-ethylaminocarbonylphenyl, 3-(N-imidazolylmethyl)phenyl, 3-(2,2,2-trifluoro-1-hydroxyethyl)phenyl, N-diethylaminocarbonylphenyl, N-protected N-propylaminocarbonylphenyl, pyridinylmethyl, aminocarbonylphenyl, 3-(H$_2$NC(=NObenzyl)-4-fluorophenyl, 3-(5-methyl-1,2,3-oxadiazolyl)phenyl, 3-(H$_2$NC(=NObenzyl)-4-fluorophenyl, benzimidazolylmethyl, benzotriazolylmethyl, indazolylmethyl, N-protected 3-ethylamino-5-indazolylmethyl, or 3-amino-5-benzisoxazolylmethyl;

m and n are independently 1, 2 or 3;

X is chloro, bromo or iodo; and

R$^3$ is a hydroxy protecting group.

5. A process of claim 1 for preparing an alkylating agent of formula (I) wherein:

Q is selected from:
phenyl substituted with 0–2 R$^{31}$;
naphthyl substituted with 0–2 R$^{31}$;
pyridyl substituted with 0–2 R$^{31}$;
pyrimidyl substituted with 0–2 R$^{31}$;
straight-chain or branched alkyl of 1–6 carbons, substituted with 0–2 R$^{31}$;

R$^{31}$ at each occurence is independently selected from: hydrogen, chloro, bromo, fluoro, alkyl of 1–3 carbons, OR$^{13}$ nitro, CF$_3$, cyano or N(R$^{13}$)(R$^{14}$);

R$^{13}$ and R$^{14}$ are independently selected from hydrogen or alkyl of 1–6 carbon atoms;

R$^3$ is a hydroxy protecting group; and

X is chloro, bromo or iodo;

m and n are independently 1, 2 or 3.

6. A process for preparing a hydroxy halide alkylating agent or an organooxy halide alkylating

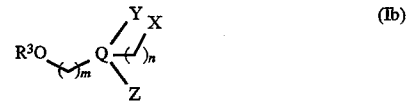
(Ib)

wherein:

Q is phenyl, naphthyl, pyridyl, pyrimidyl or straight-chain or branched alkyl of 1–6 carbons;

X is chloro, bromo or iodo;

Y and Z are independently hydrogen, chloro, bromo, fluoro, alkyl of 1–3 carbons, OR$^{14}$, nitro, CF$_3$, cyano or N(R$^{14}$)(R$^{24}$); where R$^{14}$ and R$^{24}$ independently are hydrogen or alkyl of 1–6 carbon atoms;

R$^3$ is a hydroxy protecting group; and m and n are independently 1, 2 or 3;

comprising the steps of:

(1) reacting an organodiol of formula (IIb):

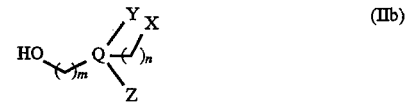
(IIb)

wherein Q, Y, Z, m and n are defined as for formula (Ib), with a halogenating reagent in a chlorinated organic solvent, with the proviso that the halogenating reagent is not a hydrogen halide, to form a compound of formula (IAb):

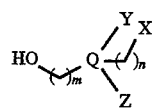

where Q, X, Y, Z, m and n are defined as for formula (Ib); and (2) reacting compound (IAb) with a reagent suitable for protecting hydroxy groups to form the compound of formula (Ib), where $R^3$ is a hydroxy protecting group.

7. A method for preparing a hydroxy halide alkylating agent or an organooxy halide alkylating agent comprising reacting an organodiol with a halogenating reagent in a chlorinated organic solvent, with the proviso that the halogenating reagent is not a hydrogen halide.

8. A process of claim 1 wherein $R^3$ is selected from: triphenylmethyl, tetrahydropyranyl, tetrahydrofuranyl, t-butyl, methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, trimethylsilyl, triethylsilyl, t-butyldimethylsilyl, t-butyldiphenylsilyl, pivaloate, or N-phenylcarbamate.

9. A process of claim 1 wherein the compound of formula (I) is obtained by carrying out steps (1) and (2) without isolation of the compound of formula (IA).

10. A process of claim 1 wherein the halogenating reagent of step (1) is selected from: thionyl halide, oxalyl halide, phosphorous pentahalide, or phosphorous oxychloride.

11. A process of claim 1 wherein the halogenating reagent of step (1) is thionyl chloride.

12. A process of claim 1 wherein the chlorinated organic solvent is selected from: chloroform, methylene chloride, tetrachloroethane, butyl chloride, or dichloroethane.

13. A process of claim 1 wherein the $R^3$ is triphenylmethyl and step (2) is carried out using acid-catalyzed triphenylmethylation.

* * * * *